(12) United States Patent
Subramaniam

(10) Patent No.: US 12,023,394 B2
(45) Date of Patent: Jul. 2, 2024

(54) VESICLE-COATED FIBERS MADE FROM CROSSLINKED LIPIDS

(71) Applicant: The Regents of the University of California, Oakland, CA (US)

(72) Inventor: Anand Bala Subramaniam, Merced, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 376 days.

(21) Appl. No.: 17/307,269

(22) Filed: May 4, 2021

(65) Prior Publication Data
US 2021/0346251 A1 Nov. 11, 2021

Related U.S. Application Data

(60) Provisional application No. 63/020,447, filed on May 5, 2020.

(51) Int. Cl.
| | | |
|---|---|---|
| A61K 8/14 | (2006.01) | |
| A61K 8/20 | (2006.01) | |
| A61K 8/55 | (2006.01) | |
| A61K 8/73 | (2006.01) | |
| A61K 8/81 | (2006.01) | |
| A61K 47/02 | (2006.01) | |
| A61K 47/24 | (2006.01) | |
| A61K 47/32 | (2006.01) | |
| A61K 47/38 | (2006.01) | |

(52) U.S. Cl.
CPC ............. *A61K 8/14* (2013.01); *A61K 8/20* (2013.01); *A61K 8/553* (2013.01); *A61K 8/731* (2013.01); *A61K 8/8117* (2013.01); *A61K 47/02* (2013.01); *A61K 47/24* (2013.01); *A61K 47/32* (2013.01); *A61K 47/38* (2013.01)

(58) Field of Classification Search
CPC . A61K 8/14; A61K 8/20; A61K 8/553; A61K 8/731; A61K 8/8117; A61K 47/02; A61K 47/24; A61K 47/32; A61K 47/38; A61K 9/5192; A61K 8/0208; A61K 8/4986; A61Q 19/08; D06M 23/12
See application file for complete search history.

(56) References Cited

U.S. PATENT DOCUMENTS

2008/0241200 A1* 10/2008 Sojka ............... A61K 8/368
424/195.17

FOREIGN PATENT DOCUMENTS

| WO | WO-9300888 A1 * | 1/1993 | ........... A61K 31/475 |
|---|---|---|---|
| WO | 2020102605 A1 | 5/2020 | |

OTHER PUBLICATIONS

Chakrabarty et al. ("Recent Advances in Nanocellulose Composites with Polymers: A Guide for Choosing Partners and How to Incorporate Them" Polymers 2018, Polymers 2018, 10(5), 517) (Year: 2018).*
Domink et al. ("Polymer Encapsulation within Giant Lipid Vesicles", Langmuir 2007 23 (13), 7148-7154) (Year: 2007).*
Akashi et al., "Preparation of giant liposomes in physiological conditions and their characterization under an optical microscope", Biophys. J. 1996, 71, 3242-3250.
Bagatolli et al., "Giant phospholipid vesicles: Comparison among the whole lipid sample characteristics using different preparation methods—A two photon fluorescence microscopy study", Chem. Phys. Lipids 2000, 105, 135-147.
Girish et al., "Fabrics of Diverse Chemistries Promote the Formation of Giant Vesicles from Phospholipids and Amphiphilic Block Copolymers", Langmuir 2019, 35, 9264-9273.
Hayward et al., "Polymerized liposomes as stable oxygen-carriers", FEBS Letters, Aug. 1985, vol. 187, No. 2, pp. 261-266.
Hupfer et al., "Liposomes from polymerizable phospholipids", Chem. Phys. Lipids 1983, 33, pp. 355-374.
Kresse et al., "Novel Application of Cellulose Paper as a Platform for the Macromolecular Self-Assembly of Biomimetic Giant Liposomes", ACS Appl. Mater. Interfaces 2016, 8, 32102-32107.
Kubsch, et al., "Phase behavior of charged vesicles under symmetric and asymmetric solution conditions monitored with fluorescence Microscopy", J. Vis. Exp. 2017, No. 128, 1-17.
Li et al., "Cellulose Abetted Assembly and Temporally Decoupled Loading of Cargo into Vesicles Synthesized from Functionally Diverse Lamellar Phase Forming Amphiphiles", Biomacromolecules, pubs.acs.org/Biomac, Dept of Bioengineering, Univ of CA, Feb. 2018, vol. 19, pp. 849-859.
Morigaki et al., "Photopolymerization of diacetylene lipid bilayers and its application to the construction of micropatterned biomimetic membranes", Langmuir 2002, 18, pp. 4082-4089.
Mueller et al., Supramolecular Materials via Polymerization of Mesophases of Hydrated Amphiphiles; NIH-PA Author Manuscript; Chem Rev. Mar. 2002 ; 102(3): 727-757.
Needham et al., "Structure and mechanical properties of giant lipid (DMPC) vesicle bilayers from 20 C below to 10 C above the liquid crystal-crystalline phase transition at 24 C", Biochemistry 1988, 27, 8261-8269.
Paul et al., "Synthesis and vesicular polymerization of novel counterion polymerizable/crosslinkable surfactants", J. Polym. Sci. Part A Polym. Chem. 2004, vol. 42, Issue 20, pp. 5271-5283.
Pazzi et al., Langmuir 2019, 35, 7798-7804.
Reeves et al., "Formation and properties of thin-walled phospholipid vesicles", J. Cell. Physiol. 1969, 73, 49-60.
Regen et al., "Polymerized Phosphatidylcholine Vesicles. Synthesis and Characterization", J. Am. Chem. Soc. 1982, 104, pp. 791-795.
Ringsdorf et al., "Molecular Architecture and Function of Polymeric Oriented Systems: Models for the Study of Organization, Surface Recognition, and Dynamics of Biomembranes", Angewandte Chemie International Edition in English, 1988, 27, pp. 113-158.http://dx.doi.org/10.1002/anie. 198801131.

(Continued)

*Primary Examiner* — Robert A Wax
*Assistant Examiner* — Quanglong N Truong
(74) *Attorney, Agent, or Firm* — Platinum Intellectual Property PC

(57) ABSTRACT

Methods and compositions for rapid and efficient assembly of substrates (e.g., fibers) coated with lamellar vesicles are provided, wherein the vesicles are more strongly attached to the substrate than those made using other methods.

32 Claims, 8 Drawing Sheets

(56) References Cited

OTHER PUBLICATIONS

Srisiri et al., "Polymerization of the Inverted Hexagonal Phase", J. Am. Chem. Soc. 1997, 119, 21, pp. 4866-4873.
Vriezema et al., "Vesicles and polymerized vesicles from thiophene-containing rod-coil block copolymers", Angew. Chemie—Int. Ed. 2003, vol. 42, Issue 7, pp. 772-776.

* cited by examiner

Figure 1
Figure 1A      Figure 1B      Figure 1C
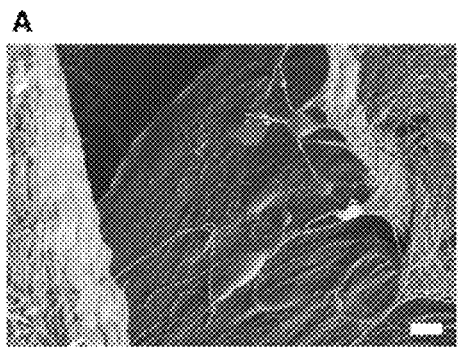 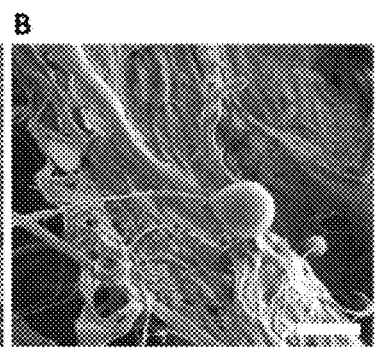 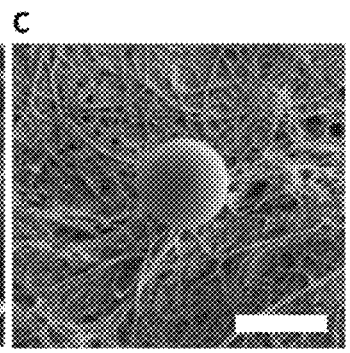
Scanning electron micrographs of cross-linked vesicles that remain stably attached to the surface of the nanopaper after drying. Scale bars A = 1 µm. B,C, 5 µm.

Figure 2
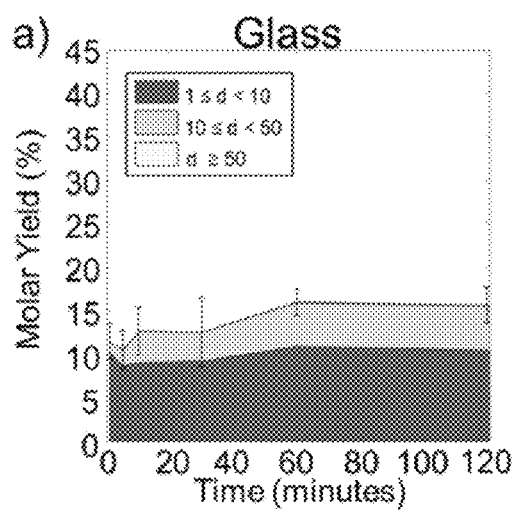
FIG. 2A
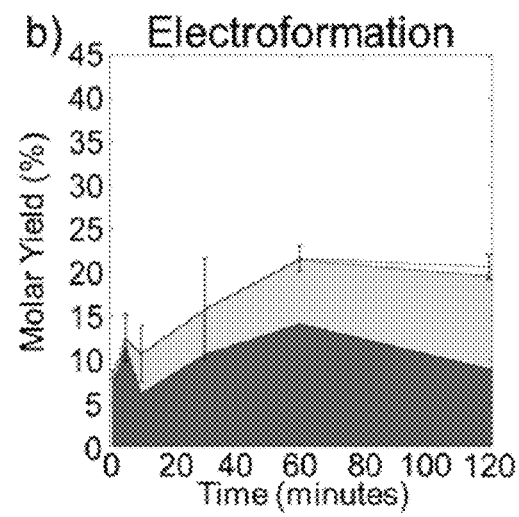
FIG. 2B
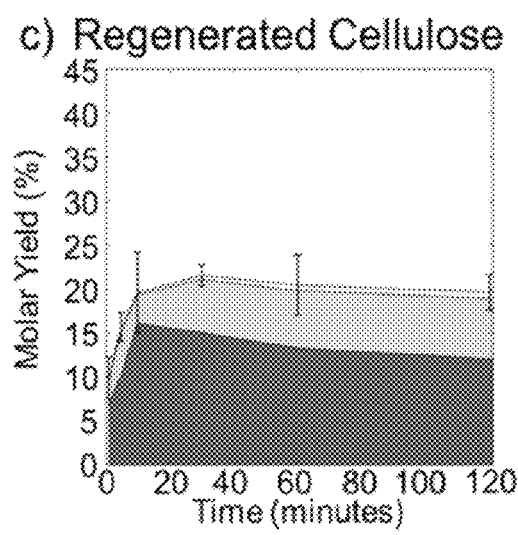
FIG. 2C
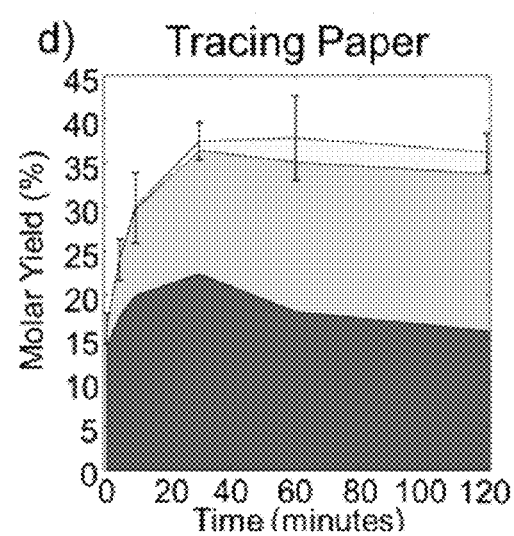
FIG. 2D

Figure 3
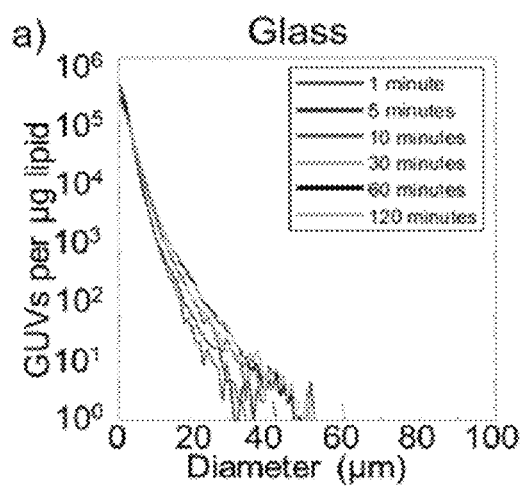
FIG. 3A
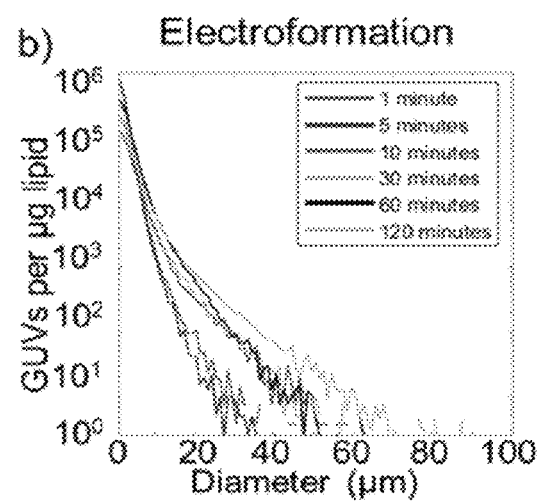
FIG. 3B
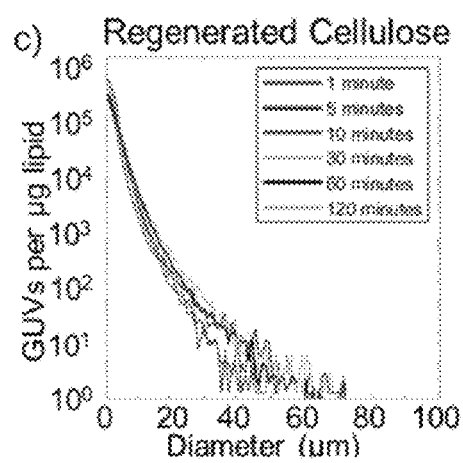
FIG. 3C
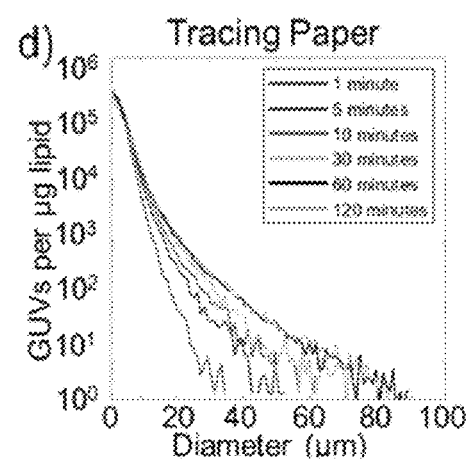
FIG. 3D

FIGURE 7
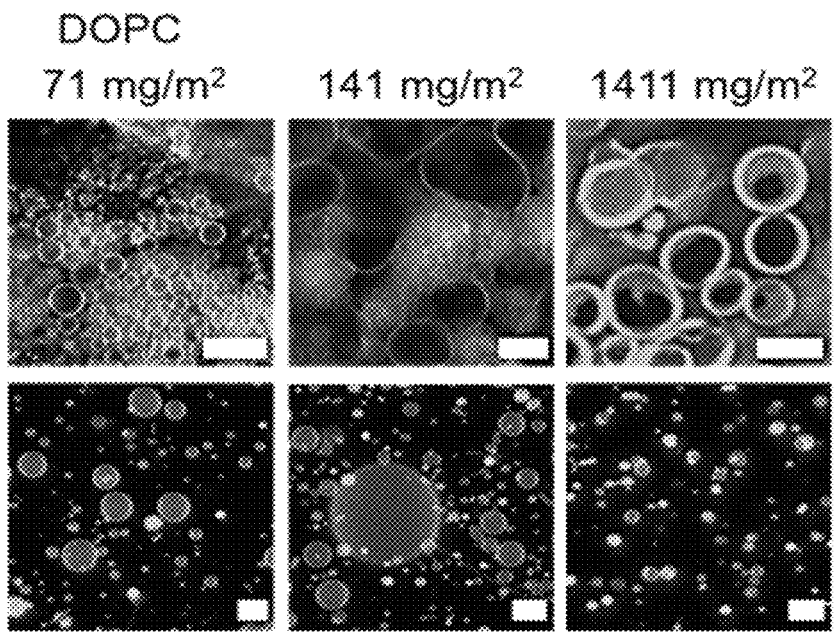
Figure 7A
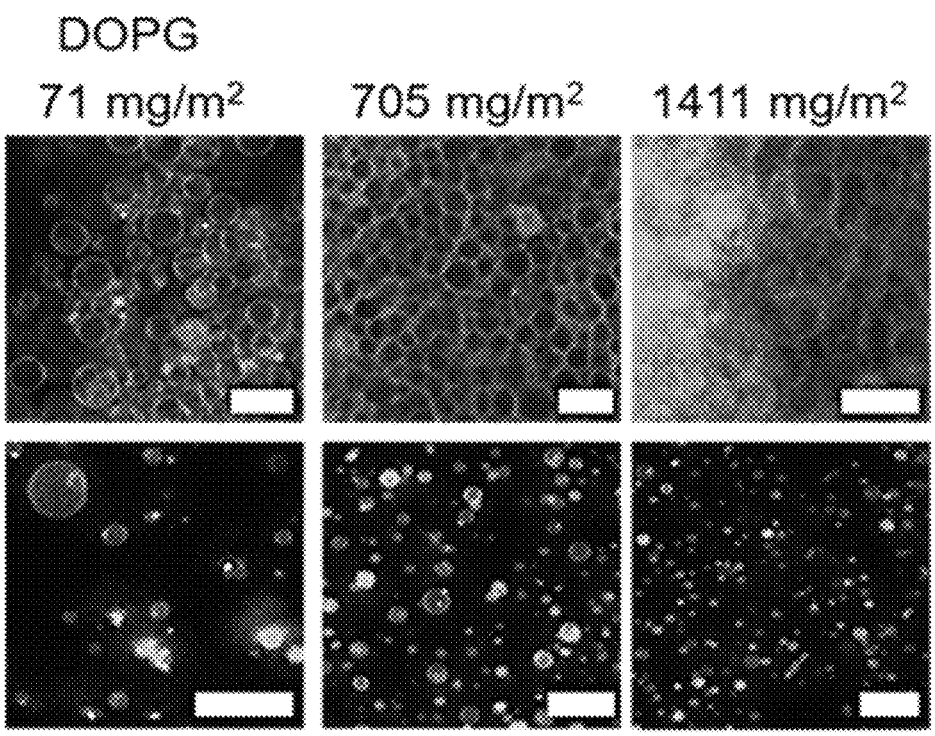
Figure 7B

FIGURE 7 (continued)
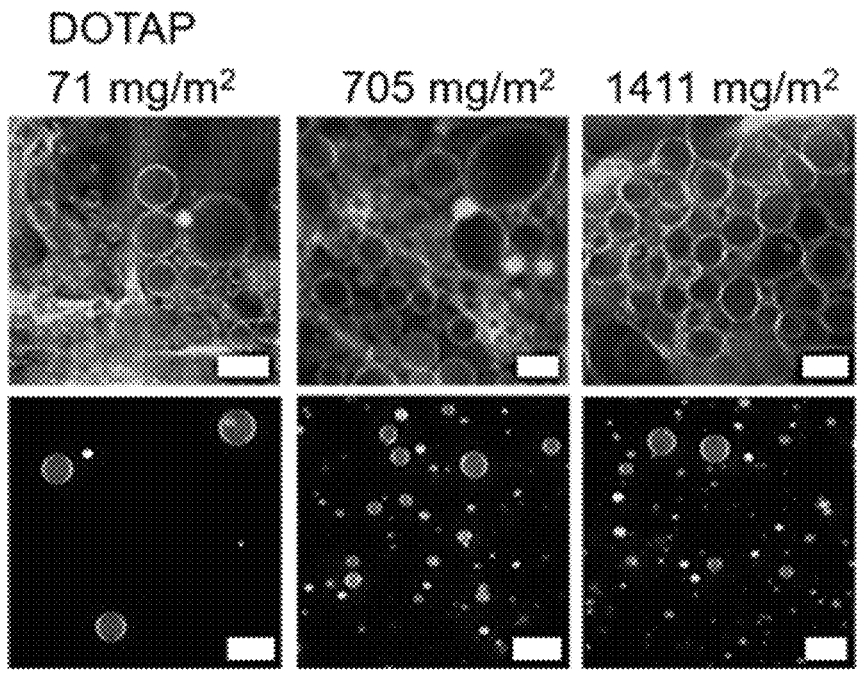
Figure 7C
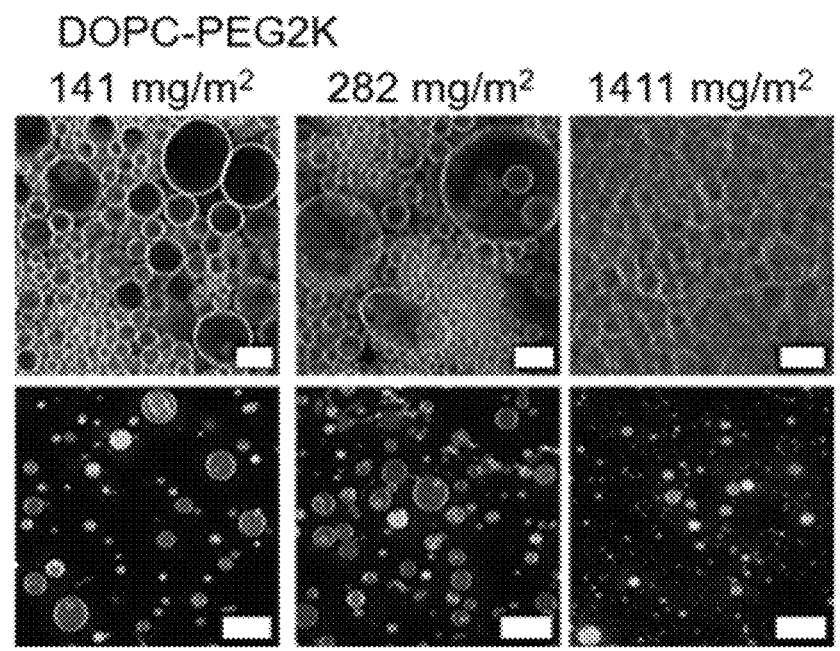
Figure 7D

VESICLE-COATED FIBERS MADE FROM CROSSLINKED LIPIDS

This application claims the benefit of U.S. Provisional Patent Application No. 63/020,447 filed May 5, 2020, the entire disclosure (including text, drawings, and photographs) of which is incorporated by reference herein, in its entirety, for all purposes.

STATEMENT REGARDING FEDERAL SUPPORT

Certain of the work described herein was conducted with federal support under contract NSF-DMR-1848573. The United States Government may have certain rights in the inventions described herein. Equipment used in some of the experiments described herein was provided through NSF MRI Award No. DMR-1625733 and NASA Grant NNX15AQ01A.

FIELD

This disclosure is in the field of biological vesicles and vesicle-coated fibers.

BACKGROUND

Various types of vesicles, containing a hydrophilic core (lumen) surrounded by a hydrophobic membrane (lamella); have found use for storing and/or dispensing both hydrophilic or hydrophobic substances, or both. Hydrophilic substances can be dispersed in the hydrophilic core of a vesicle; and hydrophobic substances can be placed in the membrane.

Giant unilamellar vesicles (GUVs) are closed phospholipid bilayer membranes (i.e., composed of a single bilayer) with diameters greater than one micrometer[1], thus mimicking the dimensions and compartmentalization properties of biological cellular membranes. GUVs are useful in vitro models for biophysical experiments. Walde, P.; Cosentino, K.; Engel, H.; Stano, P. Giant Vesicles: Preparations and Applications. Chem Bio Chem. 2010, 848-865; Dimova, R.; Aranda, S.; Bezlyepkina, N.; Nikolov, V.; Riske, K. A; Lipowsky, R. A practical guide to giant vesicles. Probing the membrane nanoregime via optical microscopy. J. Phys. Condens. Matter 2006, 18, S1151-S1176; Steer, D.; Leung, S. S. W.; Meiselman, H.; Topgaard, D.; Leal, C. Structure of lung-mimetic multilamellar bodies with lipid compositions relevant in pneumonia. Langmuir 2018, 34, 7561-7574; Dietrich, C.; Volovyk, Z. N.; Levi, M.; Thompson, N. L.; Jacobson, K. Partitioning of Thy-1, GM1, and cross-linked phospholipid analogs into lipid rafts reconstituted in supported model membrane monolayers. Proc. Natl. Acad. Sci. U.S.A. 2001, 98, 10642-10647; Veatch, S. L.; Keller, S. L. Separation of liquid phases in giant vesicles of ternary mixtures of phospholipids and cholesterol. Biophys. J. 2003, 85, 3074-3083. They are also useful for biomimetic drug delivery, and for designing synthetic cells. Roodbeen, R.; Van Hest, J. C. M. Synthetic cells and organelles: Compartmentalization strategies. Bio Essays. 2009, 1299-1308; Blain, J. C.; Szostak, J. W. Progress Toward Synthetic Cells. Annu. Rev. Biochem. 2014, 83, 615-640; Schmitt, C.; Lippert, A. H.; Bonakdar, N.; Sandoghdar, V.; Voll, L. M. Compartmentalization and Transport in Synthetic Vesicles. Front. Bioeng. Biotechnol. 2016, 4, 1-12; York-Duran, M. J.; Godoy-Gallardo, M.; Labay, C.; Urquhart, A. J.; Andresen, T. L.; Hosta-Rigau, L. Recent advances in compartmentalized synthetic architectures as drug carriers, cell mimics and artificial organelles. Colloids Surfaces B Biointerfaces 2017, 152, 199-213; Mulla, Y.; Aufderhorst-Roberts, A.; Koenderink, G. H. Shaping up synthetic cells. Phys. Biol. 2018, 15, 041001; Walde, P. Building artificial cells and protocell models: Experimental approaches with lipid vesicles. Bio Essays. 2010, 296-303; Xu, C.; Hu, S.; Chen, X. Artificial cells: from basic science to applications. Mater. Today 2016, 19, 516-532.

Lamellar stacks of phospholipids on solid surfaces such as glass or roughened Teflon spontaneously vesiculate over the course of 24-36 hours in aqueous solutions to form giant vesicles in a method known as gentle hydration. Reeves, J. P.; Dowben, R. M. Formation and properties of thin-walled phospholipid vesicles. J. Cell. Physiol. 1969, 73, 49-60; Needham, D.; Evans, E. Structure and mechanical properties of giant lipid (DMPC) vesicle bilayers from 20 C below to 10 C above the liquid crystal-crystalline phase transition at 24 C. Biochemistry 1988, 27, 8261-8269; Bagatolli, L. A.; Parasassi, T.; Gratton, E. Giant phospholipid vesicles: Comparison among the whole lipid sample characteristics using different preparation methods—A two photon fluorescence microscopy study. Chem. Phys. Lipids 2000, 105, 135-147; Akashi, K.; Miyata, H.; Itoh, H.; Kinosita, K. Preparation of giant liposomes in physiological conditions and their characterization under an optical microscope. Biophys. J. 1996, 71, 3242-3250; Kubsch, B.; Robinson, T.; Steinkühler, J.; Dimova, R. Phase behavior of charged vesicles under symmetric and asymmetric solution conditions monitored with fluorescence Microscopy. J. Vis. Exp. 2017, No. 128, 1-17.

Vesiculation can also be achieved by applying oscillating electric fields orthogonal to the lamellar phospholipid stacks in a low ionic strength environment, in a process known as electroformation. See, for example, Angelova, M. I.; Dimitrov, D. S. Liposome electroformation. Faraday Discuss. Chem. Soc. 1986, 81, 303-311.

Yet another method for forming vesicles is by hydrating lamellar phospholipid stacks on hydrogel surfaces (such as agar, dextran and polyvinyl alcohol) in a process known as gel-assisted hydration. Horger, K. S.; Estes, D. J.; Capone, R.; Mayer, M. Films of agarose enable rapid formation of giant liposomes in solutions of physiologic ionic strength. J. Am. Chem. Soc. 2009, 131, 1810-1819; Weinberger, A.; Tsai, F. C.; Koenderink, G. H.; Schmidt, T. F.; Itri, R.; Meier, W.; Schmatko, T.; Schröder, A.; Marques, C. Gel-assisted formation of giant unilamellar vesicles. Biophys. J. 2013, 105, 154-164; López Mora, N.; Hansen, J. S.; Gao, Y.; Ronald, A. A.; Kieltyka, R.; Malmstadt, N.; Kros, A. Preparation of size tunable giant vesicles from cross-linked dextran (ethylene glycol) hydrogels. Chem. Commun. 2014, 50, 1953-1955; Mora, N. L.; Gao, Y.; Gutierrez, M. G.; Peruzzi, J.; Bakker, I.; Peters, R. J. R. W.; Siewert, B.; Bonnet, S.; Kieltyka, R. E.; van Hest, J. C. M.; et al. Evaluation of dextran (ethylene glycol) hydrogel films for giant unilamellar lipid vesicle production and their application for the encapsulation of polymersomes. Soft Matter 2017, 13, 5580-5588; Movsesian, N.; Tittensor, M.; Dianat, G.; Gupta, M.; Malmstadt, N. Giant lipid vesicle formation using vapor-deposited charged porous polymers. Langmuir 2018, 34, 9025-9035; Peruzzi, J.; Gutierrez, M. G.; Mansfield, K.; Malmstadt, N. Dynamics of hydrogel-assisted giant unilamellar vesicle formation from unsaturated lipid systems. Langmuir 2016, 32, 12702-12709.

In microfluidic methods, lipids dispersed in a non-polar solvent form a double emulsion, an aqueous phase inside and an aqueous phase outside, that sandwiches a thin circular layer of the non-polar solvent using a microfluidic co-flow device. As the solvent evaporates, the lipids self-assemble to form a bilayer membrane with residual solvent left in the membrane. Dissolved solutes ("cargo") in the aqueous solution, such as small molecules, proteins, and polysaccharides can be encapsulated in the growing GUVs. Dominak, L. M.; Keating, C. D.; Dominak, L. M. Polymer encapsulation within giant lipid vesicles. *Langmuir* 2007, 23, 7148-7154; Tsai, F. C.; Stuhrmann, B.; Koenderink, G. H. Encapsulation of active cytoskeletal protein networks in cell-sized liposomes. *Langmuir* 2011, 27, 10061-10071; Dominak, L. M.; Omiatek, D. M.; Gundermann, E. L.; Heien, M. L.; Keating, C. D. Polymeric crowding agents improve passive biomacromolecule encapsulation in lipid vesicles. *Langmuir* 2010, 26, 13195-13200; Estes, D. J.; Mayer, M. Giant liposomes in physiological buffer using electroformation in a flow chamber. *Biochim. Biophys. Acta—Biomembr.* 2005, 1712, 152-160; Peterlin, P.; Arrigler, V. Electroformation in a flow chamber with solution exchange as a means of preparation of flaccid giant vesicles. *Colloids Surfaces B Biointerfaces* 2008, 64, 77-87.

New methods for the formation of vesicles, and for the deposition of vesicles onto the surface of various types of substrate, that circumvent many of the disadvantages associated with previous methods as described in the preceding paragraph, have recently been developed. Kresse et al. (2016) *ACS Applied Materials & Interfaces* 8: 32102-32107; Li et al. (2018) *Biomacromolecules* 19:849-859; Pazzi et al. (2019) *Langmuir* 35(24):7798-7804; Girish et al. (2019) *Langmuir* 35(28):9264-9273. See also International Patent Application No. PCT/US2019/061569 (filed Nov. 4, 2019), the disclosure of which is incorporated by reference, in its entirety, for all purposes. The disclosures of all of the foregoing references are incorporated by reference in their entireties for the purposes of describing methods and compositions for formation of vesicles; for depositing vesicle (e.g., GUVs) onto various types of substrates including cellulose, nanofibers, and synthetic fibers; and for the purposes of describing vesicle-coated fibers and uses thereof.

Previous methods of vesicle formation have relied on hydrophobic interactions, which drive formation of vesicles by amphiphilic molecules in an aqueous solution. Once removed from solution, however, such vesicles are unstable and prone to loss of their vesicular structure.

SUMMARY

The present disclosure provides new methods for assembling vesicles on substrates such as solid surfaces (e.g., fibers), wherein, after their formation and deposition, the vesicles are permanently attached to the substrate. The permanently-attached vesicles comprise membranes of lamellar phase amphiphiles of various sizes. Also provided are new compositions of matter comprising a composite of dried amphiphilic molecules that form lamellar phases that permanently coat the surfaces of fibers (e.g., cylindrical fibers) and woven material composed of fibers. In contrast to vesicles that are formed and deposited according to previous methods; vesicles formed and deposited according to the methods described herein are not susceptible to breakdown and/or detachment from the substrate when the vesicle-coated substrate is placed into (or removed from) an aqueous solution.

Accordingly, in certain embodiments, provided herein are methods for obtaining stable attachment of vesicles to a substrate, wherein the methods comprise dispersing an amphiphilic molecule in a solvent, wherein the amphiphilic molecule contains a crosslinkable moiety; contacting the dispersed amphiphilic molecule with the substrate; removing the solvent; incubating the amphiphile-coated substrate in a first aqueous solution; optionally removing the amphiphile-coated substrate from the first aqueous solution; and subjecting the amphiphile-coated substrate to conditions under which the amphiphilic molecules are crosslinked.

Crosslinkable moieties include, but are not limited to, tricosadiynoyl, thiophene, 11-mercaptoundecanoyl, methacrylate, methacryloyloxy, acryloyl, methacyloyl, dienoyl, sorbyl, diene monomers, diacetylenyl monomers, thiol and lipoyl. Other crosslinkable moieties are known to those of skill in the art. See, for example, Mueller & O'Brien (2002) *Chem Rev.* 102:727-757.

Amphiphilic molecules that contain crosslinkable moieties include, but are not limited to, 1-palmitoyl-2-(10,12-tricosadiynoyl)-sn-glycero-3-phosphocholine, 1,2-bis(10,12-tricosadiynoyl)-sn-glycero-3-phosphoethanolamine, 40 styrene and 50 3-(isocyano-1-alanyl-amino-ethyl)-thiophene (PS-PIAT) diblock copolymer, 1,2-bis(11-mercaptoundecanoyl)-sn-glycero-3-phosphocholine, bis[12-(methacryloyloxy)dodeca-noyl]-L-phosphatidylcholine, 1-[12-(methacryloyloxy)dodecanoyl]-2-palmitoyl-L-a-phosphatidylcholine, 1-palmitoyl-2-[12-(methacryloyloxy)dodecanoyl]-L-a-phosphatidylcholine, bis[12-(methacryloyloxy)dodeca-noyl]-L-phosphatidylcholine, 1-[12-(methacryloyloxy)dodecanoyl]-2-palmitoyl-L-a-phosphatidylcholine, 1-palmitoyl-2-[12-(methacryloyloxy) dodecanoyl]-L-a-phosphatidylcholine, bis-thiol phosphatidylcholine (bis thiol PC), bis-lipoyl phosphatidylcholine (bis-lipoyl PC) and a combination of bis-lipoyl PC with a few mole percent of a mono- or bis-thiol PC.

Conditions under which an amphiphilic molecule containing a crosslinkable moiety can be crosslinked include, but are not limited to, irradiation with ultraviolet light (e.g., light with a wavelength of 254 nm); an increase in pH (e.g., from a neutral or acidic pH to a pH above 8 (e.g., pH 8.4)); an increase in temperature; addition of $FeCl_3$ (optionally in chloroform), exposure to a free radical (e.g., hydrogen peroxide or azobisisobutyronitrile (AIBN)) optionally accompanied by an increase in temperature (e.g., to 70° C.), photopolymerization, and changes in oxidation state (e.g., oxidation, redox initiation).

In certain embodiments, tricosadiynoyl, 11-mercaptoundecanoyl, methacrylate, methacryloyloxy, and diacetylenyl monomer moieties can be crosslinked by irradiation with ultraviolet (UV) light (e.g., light having a wavelength of 254 nm).

In certain embodiments, thiophene moieties can be crosslinked by contact with $FeCl_3$ (optionally in chloroform ($CHCl_3$)) or by irradiation with ultraviolet (UV) light (e.g., light having a wavelength of 254 nm).

In certain embodiments, acryloyl and methacyloyl moieties can be crosslinked by contact with a free radical; e.g., azobisisobutyronitrile (AIBN), optionally at increased temperature (e.g., 70° C.). Additional free radicals include, for example, peroxide, superoxide, hydroxyl, hydroperoxide, peroxy radicals, hypochlorous acid and peroxynitrile.

In certain embodiments, dienoyl and sorbyl moieties, and diene monomers, can be crosslinked by irradiation with visible light (e.g., photopolymerization), change in temperature (e.g., thermal initiation) and/or changes in oxidation state (e.g., redox initiation).

In certain embodiments, thiol moieties can be crosslinked by changes in oxidation state (e.g., redox initiation) and/or by increasing pH to a value greater than pH8 (e.g., pH 8.4).

In certain embodiments, lipoyl moieties can be crosslinked by increasing pH to a value greater than pH8 (e.g., pH 8.4).

BRIEF DESCRIPTION OF THE DRAWINGS

FIG. 1A shows a scanning electron micrograph of cross-linked vesicles stably attached to the surface of a nanopaper. Scale bar=1 µm.

FIG. 1B shows a scanning electron micrograph of cross-linked vesicles stably attached to the surface of a nanopaper. Scale bar=5 µm.

FIG. 1C shows a scanning electron micrograph of cross-linked vesicles stably attached to the surface of a nanopaper. Scale bar=5 µm.

FIG. 2 contains area plots showing a time-course of molar yields of GUVs and GUV sizes using different methods. In each panel, the dark section of the bar shows the GUVs with diameters between 1 and 10 micrometers, the light section of the bar shows GUVs with diameters between 10 and 50 micrometers, and the white section of the bar shows GUVs with diameters greater than 50 micrometers. The error bars correspond to the standard deviation between the three replicates at each time point.

FIG. 2A shows results for vesicles formed on glass by gentle hydration. n=3.

FIG. 2B shows results for vesicles formed on ITO-coated glass by electroformation. n=3.

FIG. 2C shows results for vesicles formed on regenerated cellulose by gentle hydration. n=3.

FIG. 2D shows results for vesicles formed on tracing paper by gentle hydration. n=3.

FIG. 3 contains histograms of the distribution of sizes of GUVs harvested on different substrates at 1 minute, 5 minutes, 10 minutes, 30 minutes, 60 minutes, and 120 minutes. The solid lines represent the average normalized counts of GUVs harvested from each substrate (n=3) with bin widths of 1 micrometer. GUV counts are normalized per microgram of lipid harvested and only the averages are plotted for ease of viewing. Note the logarithmic scaling of the y-axis.

FIG. 3A shows results for vesicles formed on glass by gentle hydration. n=3.

FIG. 3B shows results for vesicles formed on ITO-coated glass by electroformation. n=3.

FIG. 3C shows results for vesicles formed on regenerated cellulose by gentle hydration. n=3.

FIG. 3D shows results for vesicles formed on tracing paper by gentle hydration. n=3.

FIG. 7 shows confocal images of vesicles made from optimal concentrations of lipid (center column of each panel), lower-than-optimal concentrations (left column of each panel) and higher-than-optimal concentrations (right column of each panel). For each lipid, the top row of each panel shows image of vesicles attached to the nanopaper substrate; and the bottom row shows images of vesicles after having been harvested from the substrate. FIG. 7A shows vesicles made from DOPC. FIG. 7B shows vesicles made from DOPG. FIG. 7C shows vesicles made from DOTAP. FIG. 7D shows vesicles made from DOPC doped with 5 mol % PEG-2k-PE (1,2-dioleoyl-sn-glycero-3-phosphoethanolamine-N-[methoxy(polyethylene glycol)-2000) (DOPC-PEG2K). Scale bars are 10 µm.

DETAILED DESCRIPTION

Figure 4:
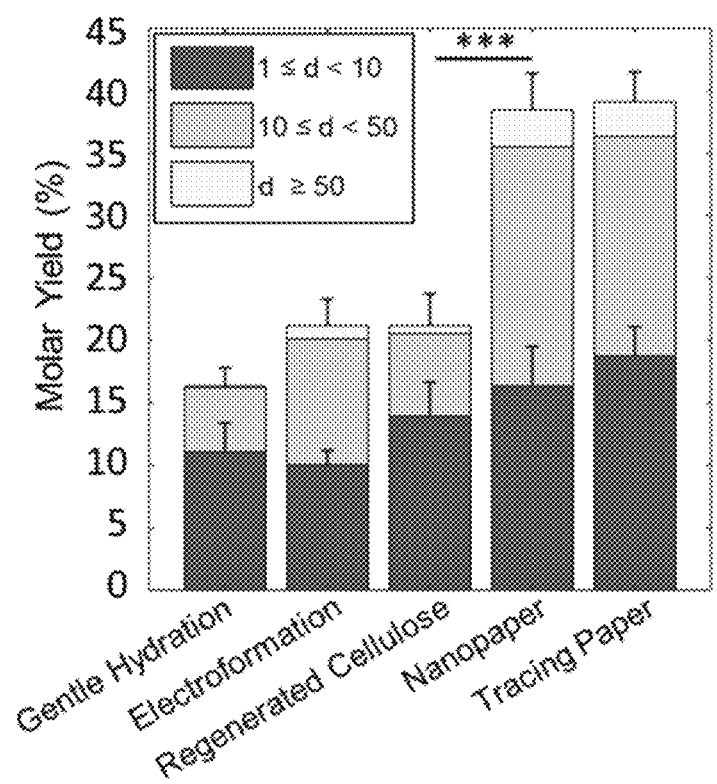
FIG. 4 is a bar graph showing the molar percent of lipid harvested as GUVs at 60 minutes of growth by gentle hydration on glass ("Gentle Hydration"), by electroformation on ITO-coated glass, and by gentle hydration on regenerated cellulose, nanocellulose paper, and tracing paper (n=5). The darkest section of each bar shows the fraction of GUVs with diameters between 1 and 10 micrometers, the lighter section of each bar shows the fraction of GUVs with diameters between 10 and 50 micrometers, and the white section of each bar shows the fraction of GUVs with diameters greater than 50 micrometers. The bottom row of error bars correspond to the standard deviation for the small GUVs and the top row of error bars show the standard deviation for the large GUVs. An ANOVA shows that nanocellulose paper and tracing paper yield a significantly higher percentage of GUVs than all of the other substrates, with a p-value less than 0.001 (***).

For the purposes of the present disclosure, the terms "amphiphile," "amphiphilic molecule" and "amphipathic molecule" all refer to a molecule that contains one or more hydrophobic regions as well as one or more hydrophilic regions, such that a population of such molecules is capable of forming lamellar structures in aqueous solution.

The term "vesicle" or "liposome" refers to a structure comprising an aqueous center bounded by one or more membranes (or lamellae). A vesicle can be bounded by a single membrane (a unilamellar vesicle), by two (concentric) membranes (a bilamellar vesicle), by three membranes (a trilamellar vesicle) or more. Vesicles can be spherical or elongated (i.e., having the shape of a solid oval) in shape. Polymeric structures comprising multiple spherical vesicles arranged in a linear polymer can also be formed using the methods described herein.

The terms "substrate" and "fiber" refer interchangeably to fibrous solids such as, e.g., cellulose, synthetic fibers, and metal meshes. In the methods described herein, amphiphilic molecules are deposited on a substrate as part of the process for forming vesicles.

The terms "nanocellulose," "nanopaper" and "nanostructured cellulose" refer to a substrate made from cellulose nanofibrils, for example, by solution casting or filtration of nanocellulose pulp.

The terms "crosslinkable moiety" and "polymerizable moiety," as used herein, refer to a chemical moiety that can be joined, under appropriate conditions, either to itself or to another polymerizable moiety. Accordingly, a molecule (e.g., a monomer) containing such a crosslinkable or polymerizable moiety can be converted to a polymer under conditions favorable to crosslinking.

The present disclosure provides, inter alia, new methods for rapid production of vesicles using fabrics (such as silk, cotton, rayon, polyester, nylon or steel wool, for example) and sheets (such as nanopaper, cellulose or dialysis membranes, for example) that are capable of forming vesicles using both positively- and negatively-charged lipids, do not require power and have minimal toxicity. The process can be summarized as follows: (1) a fabric or sheet is coated with a suitable amphiphile such as a fatty acid, a phospholipid, or an amphiphilic polymer (e.g. a diblock copolymer or a triblock copolymer) and (2) the dry, amphiphile-coated fabric or sheet is placed in contact with an aqueous solution to induce formation of vesicles. Additional amphiphiles include catanionic surfactants, bolaform amphiphiles and Archael lipids.

In additional methods, release and harvesting of vesicles from vesicle-coated substrates is achieved by fluid (e.g., an aqueous solution) flow across or through the substrate.

The disclosed methods provide the following advantages over existing methods for vesicle formation: (1) no specially-prepared substrates are required, since fabrics and paper sheets are readily available; (2) it is rapid and efficient: vesicles can be obtained within one hour and are free of contamination from substrate and solvents; and (3) the process is easily scalable since it does not require the use of either power or special equipment.

Since the methods do not require the use of power, substrates (such as, for example, fabrics and sheets as described above) can be precoated with amphiphile at a factory or other manufacturing site, then shipped dry to the point of use, at which, for example, vesicles can be harvested (by exposing the amphiphile-coated substrate to water or an aqueous solution) or the vesicle-coated substrates can be used for, e.g., cosmetic or therapeutic applications. The methods of vesicle formation are compatible with current manufacturing practices and are easily amenable to scale-up and quality control. For example, amphiphiles can be printed onto paper, akin to printing of ink, by adapting sheet making and paper coating machinery to deposit amphiphiles continuously over large areas of paper and fabric. At the site of use, another embodiment would involve providing the amphiphiles in the form of a powder that can be dissolved in a suitable solvent at the site of use prior to deposition on the substrate. Another embodiment at the site of use would involve providing the amphiphile pre-dissolved in a suitable solvent with a suitable dispersal device such as an aerosol can, an atomizer, or pipette; allowing the amphiphile to be deposited onto the substrate prior to vesicle growth.

Vesicles

Vesicles, or liposomes, as disclosed herein, contain a hydrophilic lumen and a hydrophobic membrane surrounding the lumen. Biological membranes are often made up of a repeating arrangement of amphiphilic (or amphipathic) molecules; i.e., molecules that comprise both hydrophilic and hydrophobic portions, often disposed at opposite ends of the molecule (for example, phospholipids). In aqueous solutions, amphipathic molecules arrange themselves into a bilayer such that their hydrophobic portions face each other (forming a hydrophobic core of the membrane) and their hydrophilic portions face outward toward the solvent and inward toward an aqueous lumen. The hydrophobic core of the bilayer is able to exclude charged molecules (e.g., ions) and hydrated macromolecules, while allowing passage of water and small hydrophobic molecules.

The vesicles disclosed herein are useful, inter alia, because hydrophobic molecules (e.g., drugs) can be solubilized or dispersed in the hydrophobic core of the membrane. Vesicles can then be dispersed in bulk solution, thereby increasing the availability of a hydrophobic drug dispersed in the membrane of a vesicle, compared to the availability of the same hydrophobic drug administered in non-vesicular form. In addition, vesicles can fuse with the plasma membrane of a cell (e.g., a mammalian cell, a plant cell, a bacterial cell or a fungal cell), thereby delivering cargo (either a hydrophilic molecule contained in the lumen or a hydrophobic molecule contained in the membrane) to the cell. Fungal cells, certain bacterial cells, and plant cells possess cell walls exterior to their plasma membrane; methods for breaching cells walls, thereby providing access to the plasma membrane, are known in the art. Furthermore, a receptor can be incorporated into the membrane of the vesicle to target the vesicle to a specific location (e.g., body tissue, cell type). Receptors for membrane proteins are known in the art; to provide just one example, the receptor for vascular endothelial growth factor (VEGF) is overexpressed on the surface of certain cancer cells; accordingly, VEGF or anti-VEGF receptor antibodies can be incorporated into the membrane of a vesicle to target the vesicle to a cell containing VEGF receptors in its cell membrane. Positively-charged molecules can be incorporated into the polar portion of the membrane, which will also aid in fusion of the vesicle with the negatively-charged membrane of mammalian cells.

In addition to being capable of solubilizing hydrophobic molecules in the membrane, vesicles can also encapsulate and solubilize hydrophilic molecules within their lumen. In these embodiments, encapsulated hydrophilic material is protected from the environment (e.g., blood, tissue fluid, saliva, stomach acid, etc.) until it is released from the vesicle. Disruption of the vesicle to release its luminal contents can be achieved by applying physical and chemical gradients to the vesicles, such as a gradient in osmotic pressure, a gradient in pH, and/or a gradient in temperature, any of which will cause the vesicles to burst and release their contents.

Optimal conditions for growth will vary with the type of amphiphile used to assemble the vesicle, and can include initial surface concentration of the amphiphile, pH and ionic strength of the growth buffer, and the time and temperature of incubation in growth buffer. Depending on assembly conditions, vesicles exhibit amphiphile-specific variation in size, lamellarity and structure.

Amphiphilic Molecules

Amphiphilic molecules (also known as amphipathic molecules) are compounds that contain one or more hydrophobic region(s) and one or more hydrophilic region(s) within their molecular structure. Exemplary amphiphilic molecules include phospholipids, fatty acids, sphingolipids, ceramides, fatty alcohols, quaternary ammonium surfactants, and amphiphilic polymers such as, for example, amphiphilic block copolymers (e.g., amphiphilic diblock copolymers, amphiphilic triblock copolymers). Additional exemplary amphiphilic molecules include oleic acid, phosphatidylcholine, phosphatidylglycerol, phosphatidylserine, phospatidic acid, phosphatidylethanolamine, DOPG, DOPS, DOPC, DPPC, DOPA, DOTAP, POPC, POPG, SOPC, and SOPG, for example. Biological extracts that contain amphiphilic molecules include lecithin (e.g., soybean lecithin, egg lecithin), polar extracts of any animal product containing cells or cellular organelles, such as E. coli total extract, E. coli Polar Extract, Heart Polar Extract, Liver Polar Extract, Soybean polar Extract, Egg, brain total extract and yeast polar extract. Further exemplary amphiphiles include catanionic surfactants, bolaform amphiphiles and Archael lipids.

Additional exemplary amphiphiles include DOPC:TopFluor-Cholesterol, DOPC:Rhodamine-DPPE, ESM:DOPC: Chol:TopFluor-Cholesterol: Rhodamine-DPPE, DPPC:TopFluor PC, DOPS:DOPC:TopFluor-Cholesterol, POPG: TopFluor-Cholesterol, DOTAP:TopFluor-Cholesterol, didodecyldimethylammonium bromide (DDAB), myristoleic acid, Dodecyltrimethylammonium bromide (DTAB), and Didodecyldimethylammonium bromide (DDAB).

Substrates

Using the methods disclosed herein, vesicles (e.g., liposomes, GUVs) can be deposited on a substrate and the vesicle-coated substrates can be used as disclosed elsewhere herein. Substrates for use in the disclosed methods include, but are not limited to fibers (e.g., curved fibers, cylindrical fibers, flattened cylindrical fibers, wavy cylindrical fibers or linear poly-spherical fibers) and metal mesh (e.g., stainless steel, copper or steel wool). Fibers include naturally-occurring fibers, such as cellulose, silk and wool. Cellulose fibers include papyrus, paper, wood pulp, cotton, hemp and jute. Fibers also include synthetic fibers, such as, for example, nylon and polyester and semi-synthetic fibers such as, for example, rayon. Fibers also include inorganic synthetic fibers such as, for example, fiberglass. Fibers also include nanofibers, such as tracing paper, nanocellulose paper (i.e., nanostructured cellulose paper), or regenerated cellulose membrane (e.g., dialysis membrane).

Fibers can also include three dimensional tissue culture scaffolds, and bandages such as polycaprolactone (PCL) nanofibers and collagen nanofibers. Collagen can be derived from rat's tail and decellularized bovine myocardium. Nanocellulose can be derived from, e.g., plant biomass, bacteria, algae and tunicates. Fibers can be randomly enmeshed (e.g., paper), woven (e.g., fabrics such as cotton), non-woven (e.g., felt) or aligned in certain directions. For the purposes of this disclosure, the terms "fiber" and "fabric" are used interchangeably.

Cellulose is an abundant biopolymer that is both hygroscopic and hydrophilic, yet it is essentially insoluble in water and most organic solvents, even at elevated temperatures. As disclosed herein, hydrating dried lipid films on cellulose provides a facile route to preparing vesicles (e.g., giant liposomes) that are predominantly unilamellar; i.e., giant unilamellar vesicles (GUVs). Without wishing to be bound by theory, it is likely that curvature of cellulose fibers, along with the swelling of cellulose fibers upon exposure to water provides a driving force for separating the lamellae, present in hydrated multilayer lipid stacks, into unilamellar vesicles. The use of cellulose as a substrate for the production of vesicles, such as liposomes, is a significant departure from current methods (utilizing, e.g., Teflon, electric fields, etc.), and greatly simplifies procedures for fabricating biological vesicles.

As described herein, the curvature of the elements (e.g., fibers, fibrils) within a substrate is positively correlated with the yield of vesicles obtained on that substrate using the methods described herein. Flat substrates such as glass, which has a radius of curvature=0, provide a low yield of vesicles. For an outwardly curved linear fiber or fibril, which provides a higher vesicle yield, one principal radius of curvature is >0. Fibers can also be curved inward (i.e., concave or collapsed fibers), in which case the radius of curvature is <0. In addition, a fiber containing a collection of spheres (e.g., a string of spheres), which would have two principal non-zero radii of curvature, will also provide high yields of vesicles.

In certain embodiments, fibers or fibrils have dimensions (e.g., length, diameter) in the nanometer range; e.g., nanofibers or nanoscale fibers.

In certain embodiments, nanocellulose paper is used as a substrate. Plant-derived cellulose fibers have a hierarchical structure. Smook, G. Handbook for Pulp and Paper Technologists. (TAPPI Press, 2016). Cellulose fibers are tens of micrometers in diameter and are composed of microfibrils which themselves contain bundles of hydrogen-bonded nanofibrils having a diameter of approximately 5-60 nm. See Klemm et al. (2011) *Angew. Chemie-Int. Ed.* 50:5438-5466. Chemical hydrolysis and high-pressure mechanical homogenization defibrillates plant-derived cellulose fiber pulp into nanocellulose pulp. Klemm et al., supra. Nanocellulose pulp can be converted to nanocellulose paper by, e.g., solution casting or filtration. Nanocellulose can also be obtained from cellulose-producing bacteria, albeit in smaller quantities and at higher costs. Klemm et al., supra.

Cellulose nanofibrils can obtained from cellulose fibers through mechanical homogenization using shear, pressure, and/or chemical treatments. See, for example, Li Y-Y et al. (2018). Review of Recent Development on Preparation, Properties, and Applications of Cellulose-Based Functional Materials. *Int J Polym Sci.;* 2018:1-18. doi:10.1155/2018/8973643. The water is allowed to evaporate at room temperature, leaving behind a thin sheet of nanopaper. The nanopaper is rinsed and cleaned thoroughly with chloroform and then water. Alternately commercial tracing paper, which is also mechanically and chemically refined to obtain a dense fibrillar surface, can be used.

Additional exemplary substrates include three-dimensional tissue culture scaffolds, bandages such as polycaprolactone (PCL) nanofibers, collagen nanofibers, and extracellular matrix fibers (i.e., decellularized extracellular matrix).

Vesicle Formation

Vesicles are formed by applying a dispersion of an amphiphilic molecule to a substrate (e.g., a fiber such as cellulose) and allowing the dispersed amphiphile to dry onto the substrate; e.g., by evaporation of the solvent in which the amphiphile is dispersed, followed by contact of the dried, amphiphile-coated substrate with an aqueous solution (i.e., a "growth buffer"). After deposition of amphiphile onto a substrate and evaporation of the solvent, the amphiphile forms deposits on the surface of the substrate. Contact of the amphiphile-coated substrate with water (or with an aqueous solution) causes the amphiphile deposit to rearrange into stacks that form vesicles.

Any solvent in which a particular amphiphile can be dispersed can be used. It is straightforward to determine whether a particular solvent is capable of dispersing a particular amphiphile. Suitable solvents in which an amphiphile can be dispersed include both polar and nonpolar solvents. For example, a suitable solvent can be an alkane such as, e.g., pentane, hexane or octane; an aromatic solvent such as, e.g., chloroform, toluene, benzene, carbon tetrachloride, acetone, methylene chloride, xylene or squalene; an alcohol, such as, e.g., methanol, ethanol, isopropanol and higher alcohols; acetone, or water.

Vesicles made by the methods disclosed herein can be unilamellar or can comprise multiple (e.g., concentric) membranes. The degree of lamellarity (i.e., unilamellar, multilamellar) of vesicles made by the methods described herein (or the formation of other structures such as multivesicular structures and amphiphile droplets) is correlated with the thickness of the layer of amphiphile that is deposited on the substrate. In general, unilamellar vesicles are produced from amphiphile layer thicknesses of 1-50 bilayer stacks; corresponding to 10-100 micrograms amphiphile applied to a circular disc of substrate 9.5 mm in diameter. Formation of multilamellar vesicles requires on the order of 100 or more bilayer stacks of amphiphile on the substrate; corresponding to a mass of amphiphile of 100 micrograms or greater applied to a 9.5 mm diameter disc of substrate. These guidelines can be extrapolated, by converting the above guidelines into amphiphile mass/substrate surface area values, to provide guidelines for formation of uni- and multi-lamellar vesicles on non-circular substrates.

Growth Buffers

Formation of vesicles on lipid- or amphiphile-coated substrates occurs when the dried, coated substrate is placed in an aqueous "growth buffer." Choice of growth buffer depends on factors such as, e.g., vesicle size, vesicle cargo, and the nature of the lipid or amphiphilic molecule used to assemble the membrane of the vesicle. Growth buffers can range from water (e.g., distilled water, ultrapure water) to sugar solutions (e.g., sucrose) to ionic buffers such as, for example, Tris-buffered saline (TBS), 4-(2-hydroxyethyl) piperazine-1-ethanesulfonic acid (HEPES) or phosphate-buffered saline (PBS). Biological fluids such as, for example, blood, plasma, serum, tears, urine and saliva can also be used as growth buffers.

Vesicle Loading

When dispersed in growth buffer, macromolecules such as proteins and polysaccharides (i.e., cargo) are spontaneously incorporated from solution into the lumen of the vesicle. For certain amphiphiles, elevated temperatures (i.e., temperatures above room temperature) may be required for vesicle assembly. In these cases, vesicle formation can be temporally uncoupled from loading of cargo by coating substrate with amphiphile at elevated temperature (e.g., 80° C.) in the absence of cargo, cooling the amphiphile-coated substrate to room temperature or below, and contacting amphiphile-coated substrate with an aqueous solution of the cargo molecule(s).

Loading of cargo from solution into vesicles is has a diffusion-driven component; dependent on the concentration of the cargo molecule, the diffusion coefficient of the cargo molecule and the size of the vesicles. In certain embodiments, the concentration of cargo in the loading solution is on the order 1 µM. In additional embodiments, the concentration of cargo molecule can be between 0.5 and 2 µM, or between 0.1 and 5 µM, or between 1 and 10 µM. For a cargo molecule with a diffusion coefficient of $10^{-11}$ $m^2$ $s^{-1}$, the characteristic time for diffusion of the molecule into vesicles is about 10 s. In certain embodiments, loading times of 10 sec, 30 sec, 1 min, 5 min, 10 min, 20 min 30 min and 1 hr can be used.

For loading of hydrophobic molecules, the molecules can be added directly to a dispersion of amphiphile in solvent prior to coating the substrates. Alternately hydrophobic cargo can be deposited on the substrate either before or after depositing the amphiphile. After preparing the coated substrate, hydrophobic cargo will partition into the hydrophobic region of the bilayer membranes immediately upon hydration.

To provide just one example, the hydrophobic dye Nile Red is sparingly soluble in water, but is highly soluble in chloroform. Accordingly, Nile Red can be mixed with an amphiphile (e.g., a lipid) prior to deposition of the amphiphile on a substrate. Upon vesicle formation (e.g., after contacting a Nile Red/lipid-coated fiber with water), the Nile Red, trapped in the membrane of the vesicles, adheres to the fiber but is insoluble in the growth buffer. Accordingly, the fibers fluoresce brightly in a non-fluorescent background of growth buffer. Optionally, vesicles can then be detached from the fiber, carrying the Nile Red (still trapped in the vesicle membranes) from the fibers into the aqueous phase.

Hydrophilic cargo can also be deposited on the substrate for simultaneous dissolution and loading into the vesicles. For example, the polysaccharide dextran is highly soluble in water. An aqueous solution of a hydrophilic molecule (e.g., a polysaccharide such as dextran) can be deposited on a substrate and allowed to dry. An amphiphile can then be deposited onto the substrate containing the dried hydrophilic molecule. Upon vesicle formation, the hydrophilic molecule (e.g., dextran) is dissolved in the solution (i.e., the growth buffer) and is encapsulated into the lumens of the vesicles.

Controlled Vesicle Formation and Release

When amphiphile is deposited onto a substrate using the methods and compositions disclosed herein, it forms lamellar stacks of amphiphile. Upon contact with water or aqueous solutions, these stacks spontaneously vesiculate. For certain applications, it is desirable to prevent or delay vesiculation, while maintaining the substrate in an aqueous environment; then trigger vesiculation at a later time.

Accordingly, methods to delay and then trigger vesiculation from an amphiphile-coated substrate in aqueous solution are provided. The methods are based on the fact that solutions with high osmotic pressure prevent vesiculation. Accordingly, an amphiphile-coated substrate is hydrated in aqueous solutions containing a dissolved substance (osmolyte) that exerts an osmotic pressure greater than 1 kPa, which prevents vesiculation. Such a condition can be achieved by using a solution of, for example, 2 mM Ficoll 400. Vesicle formation can then be triggered by diluting the osmolyte to a concentration that allows vesiculation; e.g., that results in an osmotic pressure below 1 kPa (which corresponds to a concentration of 0.7 mM Ficoll 400 or less), which causes vesicles to form.

Additional osmolytes that can be used in these methods include, but are not limited to casein, bovine serum albumin (BSA), dextrans (e.g., Dextran 100,000, Dextran 6,000), polyvinylpyrrolidones (e.g., PVP 3500, PVP 800, PVP 350), and polyethylene glycols (e.g., PEG 3000, PEG 600, PEG 400). Conditions for inhibition and induction of vesicle formation will differ for different osmolytes.

Applications of this method include shipping amphiphile-coated substrates in wet (osmolyte-containing) pouches in an activated state (for example to preserve the function of sensitive protein or drugs) and then placing the coated substrate into a solution lacking osmolyte to trigger vesiculation.

Vesiculation can also be controlled by temperature. In these methods, amphiphile-coated substrates are hydrated in aqueous solutions below the transition temperature of the amphiphile. When below the transition temperature, the amphiphile does not vesiculate on the substrates. Such a condition can be achieved for example by using as an amphiphile 1,2-dipentadecanoyl-sn-glycero-3-phosphocholine which has a transition temperature of 35° C. Upon increasing the temperature above 35° C., for example by placing the amphiphile-coated substrate in contact with the human body, which has a temperature of 37° C., vesicles are formed. Amphiphile-coated substrates can thus be shipped in an activated state and then vesiculation triggered when suitable temperature conditions are achieved.

Additional amphiphiles are described elsewhere herein, and the transition temperatures of amphiphiles are known in the art.

Manufacturing

The methods disclosed herein for vesicle assembly onto fibers are compatible with the production of large numbers of vesicles in a centralized manufacturing facility. Fabrics and papers are routinely processed using large machines, e.g., for drying, printing, washing, etc. Accordingly, batch processing methods and assembly line procedures for obtaining vesicles are feasible using the methods disclosed herein. Such large-scale methods are impractical and/or prohibitively expensive using current procedures for manufacturing vesicles. The fact that fabrics are reusable (see Example 6) is also consistent with large-scale manufacturing of vesicles using the methods described herein.

Therapeutic Compositions and Therapeutic Applications

In certain embodiments, vesicle-coated fibers (e.g., silk, cotton) provide therapeutic compositions for use as bandages containing, e.g., analgesic, anesthetic, antibiotic (e.g., antimicrobial, antifungal) and/or antiviral compounds. Both hydrophilic and/or hydrophobic compounds can be contained in such compositions. Hydrophilic compounds are encapsulated in the lumens of vesicles, where they remain protected from the environment, and from drug-deactivating molecules that can be released by certain infectious microorganisms, until release is triggered.

Release can be triggered, for example, by wetting the bandage with water or an aqueous solution such as saline or PBS, or by contact with bodily fluids in the wound. Release can also be triggered by changes in the temperature of the wound compared to the surrounding tissue, (e.g., due to inflammation and/or infection), and/or changes in pH in the wound compared to the surrounding tissues.

Depending on vesicle size, degree of lamellarity of the vesicle, lipid (or amphiphile) composition of vesicle, shape of the vesicle, diffusion coefficient of the compound, partition coefficient of the compound, temperature, and the presence or absence of flow, the release rate of the compound(s) into a wound can be controlled. Various types of targeting molecules (e.g., lectins, antibodies, nanobodies, FAB fragments, protein receptors or ligands, Annexin V) can be incorporated into vesicle membranes to direct the vesicle to a particular cell or tissue in a subject.

The chemotherapeutic agents doxorubicin and taxol are examples of hydrophobic drugs that can be transported and delivered by vesicles as described herein. These compounds have molecular characteristics similar to those of Nile Red, such as fused planar cyclic rings, and thus possess similar loading characteristics. Release of these drugs occurs when the vesicle membranes fuse with the plasma membrane of target cells, or when the vesicles are taken up (e.g., endocytosed) by the target cells.

Additional exemplary therapeutic cargo molecules include viruses (which can be used a vectors for gene delivery), bacteriophages (which can be used as anti-bacterial agents for, e.g., treatment of infections by antibiotic-resistant bacteria) and silver nanoparticles (which can also be used as anti-bacterial agents).

Additional therapeutic compositions include stents (e.g., for delivery of an anticoagulant compound), suppositories, pessaries (e.g., for delivery of a contraceptive compound) and sublingual applicators.

Cosmetic Compositions and Cosmetic Applications

As noted, vesicles can be used as carriers of both hydrophilic substances (in their lumen) and/or hydrophobic substances (in their membrane). In certain embodiments, the vesicle-coated fabrics disclosed herein are used as applicators (e.g., skin patches, face masks) for cosmetic agents. Human skin has a hydrophobic barrier, and liposomal formulations have been shown to increase transport of hydrating molecules and other adjuvants into deeper skin layers.

Accordingly, in one embodiment for providing anti-aging cosmetics, the disclosure provides vesicle-coated silk sheets wherein the vesicles contain an anti-aging agent such as, for example, retinol. Retinol, being a hydrophobic compound, is incorporated into vesicle membranes by, for example, co-dispersing retinol with an amphiphile in a solvent, applying the liquid to a substrate such as cotton or silk, and drying.

Thus, retinol-coated silk face masks for skin treatment are provided. Application of the mask (e.g., to the face) followed by moistening and/or gentle agitation of the mask will release the retinol onto the skin of the subject.

In additional embodiments for dermal rejuvenation, vesicle-coated fibers, in which the vesicles contain ceramides in their membranes, are used. Many skin lipids are composed of high-melting temperature ceramides that are solid at room temperature and therefore difficult to transport into skin. Dispersing such ceramides in the vesicle membrane will facilitate incorporation of the ceramide(s) into the skin.

Substrates can be coated with amphiphiles by dissolving amphiphile in a suitable solvent or mixtures of solvents (for example, methanol, grain alcohol, acetone, water and/or mixtures thereof), then applying the amphiphile to a fabric or other substrate by using, for example, an aerosolizer, nebulizer, or spray bottle.

Accordingly, additional compositions include vesicle-coated fabrics (e.g., performance fabrics for use in sports and exercise) containing antiperspirants and/or fragrances. In these embodiments, a cosmetic molecule (e.g., an antiperspirant and/or a fragrance) is loaded into vesicles, as described herein, and the loaded vesicles are formulated as a spray or aerosol which can then be applied to a fabric (e.g., an article of clothing made from any naturally-occurring or synthetic fabric as disclosed herein). Thus, in these embodiments, the article of clothing serves as the substrate and antiperspirant-containing and/or fragrance-containing vesicles are formed on the article of clothing. Upon wetting of the fabric, either by perspiration or dousing with water or an aqueous solution, the cargo molecules (e.g., antiperspirant, fragrance) are released from the clothing.

Other compounds such as, for example, sunscreens, insect repellants, antibacterial compounds (to control bacterial odors), humectants (for skin hydration), nicotine and performance-enhancing drugs can also be incorporated into clothing in similar fashion.

In additional embodiments, a spray or aerosol in which the vesicles contain a fragrance and/or an antiperspirant can be sprayed onto the skin of a subject wherein, upon perspiration, vesicles are released and deliver the fragrance and/or antiperspirant.

Additional Applications

Cellulose and nanocellulose can be used in a variety of biomedical and pharmaceutical areas such as, for example, drug delivery, tissue engineering, wound healing, contact lenses, artificial blood vessels, hemodialysis and manufacture of protein-based pharmaceuticals; due to their nontoxicity, biodegradability, structural strength and thermal stability. The ability to deposit vesicles onto these cellulosic and nanocellulosic materials will further expand their utility in these areas. For example, cellulosic bandages can be loaded with vesicles containing analgesic, anesthetic and/or antibiotic compounds. Stents or other intravascular inserts can be coated with vesicles containing anticoagulants, statins or other cholesterol-lowering agents and/or blood pressure medication. The flow of blood causes a fluid shear stress that can transport the vesicles from the stents to clots or other restrictions. Materials used in tissue engineering can be coated with vesicles containing, e.g., growth factors, growth inhibitors, and/or ATP. In addition, because vesicles are similar sizes to cells, vesicles can serve as a mimic to cells to provide contact stimulus or scaffolds.

Vesicles as disclosed herein are self-assembled macromolecular structures useful for encapsulating and controlling the release of cargo, synthesizing proteins (e.g., by cell-free synthesis) and inorganic minerals (e.g., by biomineralization), constructing artificial cells (e.g., red blood cells, building nanoconduits, nanowires, and nanoparticles through bioinspired templating strategies, and elucidating the origins of life through the construction of minimal protocells. Vesicles (e.g., giant liposomes) are also widely used model systems for biochemical and biophysical studies of membrane processes.

Functionalization of Substrates Using Crosslinked Lipids

Formation of vesicles by amphiphiles is governed by hydrophobic interactions, which exist only when amphiphiles are surrounded by aqueous solution. Thus, when the solution dries, or when an aqueous phase is replaced with an organic solvent, the vesicles are destabilized and revert to their constituent amphiphile molecules. Fibers can be coated with more stable vesicles, that resist the action of solvents and drying, by forming the vesicles from amphiphiles containing crosslinkable moieties attached to either the headgroup (i.e., the hydrophilic portion of the amphiphile) or the tail (i.e., the hydrophobic portion of the amphiphile). Such crosslinkable amphiphiles are deposited on a substrate, and vesicles are allowed to form by any of the methods described herein or known in the art. After formation of the vesicles on the substrate, the amphiphile molecules are crosslinked, resulting in more stable attachment of the vesicles to the substrate.

Crosslinking can be induced by, for example, application of specific types of energy (e.g., irradiation such as photopolymerization or ultraviolet irradiation), chemical catalysts (e.g., iron, free radicals), or environmental triggers such as pH, ionic strength, temperature, osmolarity and oxidation state. Alternately, the vesicles can be released from the fibers prior to the cross-linking procedure and polymerized in solution.

Polymerizable moieties that can be attached to, or that are present on, certain amphiphilic molecules, include, for example, tricosadiynoyl, 11-mercaptoundecanoyl, methacrylate, methacryloyloxy, acryloyl, methacyloyl, dienoyl, sorbyl, diene monomers, diacetylenyl monomers, thiol, lipoyl and thiophene. Exemplary polymerizable moieties, and methods for their polymerization, are shown in Table 1. Table 2 provides examples of amphiphilic molecules that contain polymerizable moieties.

TABLE 1

Polymerizable moieties and methods for their polymerization

| Polymerizable moiety | Polymerization method |
|---|---|
| tricosadiynoyl | UV irradiation |
| thiophene | Addition of (FeCl$_3$) in CHCl$_3$ |
|  | UV irradiation |
| 11-mercaptoundecanoyl | UV irradiation |
| methacrylate | UV irradiation |
| methacryloyloxy | UV irradiation |
| acryloyl | Free radical-induced (e.g., azobisisobutyronitrile (AIBN) at 70° C.) |
| methacyloyl | Free radical-induced (e.g., azobisisobutyronitrile (AIBN) at 70° C.) |
| Dienoyl | Photopolymerization (e.g., 254 nm) Thermal initiation (e.g. 70° C.) Redox initiation (e.g., more reducing conditions) |
| Sorbyl | Photopolymerization (e.g., 254 nm) Thermal initiation (e.g. 70° C.) Redox initiation (e.g., more reducing conditions) |

TABLE 1-continued

Polymerizable moieties and methods for their polymerization

| Polymerizable moiety | Polymerization method |
|---|---|
| Diene Monomers | Photopolymerization (e.g., 254 nm) Thermal initiation (e.g. 70° C.) Redox initiation (e.g., more reducing conditions) |
| Diacetylenyl Monomers | UV irradiation |
| Thiol | Oxidation |
| Lipoyl | Increase pH to 8.4 |
| Thiol | Increase pH to 8.4 |

TABLE 2

Amphiphiles containing polymerizable moieties

| Amphiphile | Polymerizable moiety |
|---|---|
| 1-palmitoyl-2-(10,12-tricosadiynoyl)-sn-glycero-3-phosphocholine | tricosadiynoyl |
| 1,2-bis(10,12-tricosadiynoyl)-sn-glycero-3-phosphoethanolamine | tricosadiynoyl |
| 40 styrene and 50 3-(isocyano-1-alanyl-amino-ethyl)-thiophene (PS-PIAT) diblock copolymer | thiophene |
| 1,2-bis(11-mercaptoundecanoyl)-sn-glycero-3-phosphocholine | 11-mercaptoundecanoyl |
| bis[12-(methacryloyloxy)dodeca-noyl]-L-phosphatidylcholine | methacrylate |
| 1-[12-(methacryloyloxy)dodecanoyl]-2-palmitoyl-L-a-phosphatidylcholine | methacrylate |
| 1-palmitoyl-2-[12-(methacryloyloxy)dodecanoyl]-L-a-phosphatidylcholine | methacrylate |
| bis[12-(methacryloyloxy)dodeca-noyl[-L-phosphatidylcholine | methacryloyloxy |
| 1-[12-(methacryloyloxy)dodecanoyl]-2-palmitoyl-L-a-phosphatidylcholine | methacryloyloxy |
| 1-palmitoyl-2-[12-(methacryloyloxy)dodecanoyl]-L-a-phosphatidylcholine | methacryloyloxy |
| bis-thiol PC | thiol |
| bis-lipoyl PC and a few mole percent of a mono- or bis-thiolPC | Lipoyl and thiol |

Other polymerizable moieties, and methods for their polymerization, are known in the art. See, for example, Mueller & O'Brien (2002) *Chemical Reviews* 102:727-757; Ringsdorf et al. (1988) *Angew. Chem. Int. Ed. Engl.* 27:113-158.

Crosslinked lipid structures are more resistant to solvents and shear forces, and possess longer shelf lives. Regen, S. L. et al., Polymerized Phosphatidylcholine Vesicles. Synthesis and Characterization, *J. Am. Chem. Soc.* 1982, 104, 791-795; Hupfer, B. et al., Liposomes from polymerizable phospholipids, *Chem. Phys. Lipids* 1983, 33, 355-374. In addition, a wide array of polymerizable lipids is available, suitable for a number of different applications. Vriezema, D. M. et al., Vesicles and polymerized vesicles from thiophene-containing rod-coil block copolymers, *Angew. Chemie-Int. Ed.* 2003, 42, 772-776; Hayward, J. A. et al., Polymerized liposomes as stable oxygen-carriers, *FEBS Lett.* 1985, 187, 261-266. Lipids with polymerizable headgroups such as diacetylene have been demonstrated to polymerize in the presence of UV light. Morigaki, K. et al., Photopolymerization of diacetylene lipid bilayers and its application to the construction of micropatterned biomimetic membranes, *Langmuir* 2002, 18, 4082-4089. Lipids with reactive vinyl counterions have been polymerized in their vesicular form. Paul, G. K. et al., Synthesis and vesicular polymerization of novel counter-ion polymerizable/crosslinkable surfactants,

*J. Polym. Sci. Part A Polym. Chem.* 2004, 42, 5271-5283. The foregoing results demonstrated increased stability of vesicles in the presence of detergents and organic solvents such as ethanol. Furthermore, inter-vesicular polymerization was also observed, enabling the formation of chains of vesicles. Various other phases of lipids can also be stabilized, providing a means to produce stable, lipid liquid crystalline phases. Srisiri, W. et al., Polymerization of the inverted hexagonal phase, *J Am. Chem. Soc.* 1997, 119, 4866-4873. Crosslinking thus offers a means for functionalization of fabrics with lipid molecules, by using polymerization to attach lipids, either as bilayers or as vesicles tethered to the surface through polymer chains.

The more stable attachment of vesicles to fibers, as disclosed herein, alters certain physical properties of the fiber, for example, by increasing the available surface area of the fiber; which can be important for processes such as catalysis, filtration and capture. For example, if vesicles contain encapsulated nanoparticles or other materials, such particles can be more strongly, in some cases permanently, attached to a fiber.

EXAMPLES

Example 1: Vesicle Formation on Nanopaper by Polymerization of Lipid: 1-palmitoyl-2-(10,12-tricosadiynoyl)-sn-glycero-3-phosphocholine In this example, fibers were functionalized with amphiphiles that can be cross-linked. 10 μL of a 1 mg/mL solution of 1-palmitoyl-2-(10,12-tricosadiynoyl)-sn-glycero-3-phosphocholine in chloroform was placed onto a circular piece of nanocellulose paper 9.5 mm in diameter. The chloroform was allowed to evaporate. The nanopaper was incubated in 150 μL of water for 60 minutes; removed from the water, then exposed to 254 nm UV light for 20 minutes; using a small low-pressure mercury lamp (2 W, UVP, Pen-Ray, Upland, CA). The paper was then dried and imaged by scanning electron microscopy. FIGS. 1A, 1B and 1C show that vesicles are present on the surface of the paper.

Papers are placed in water again and samples are removed at various time points from 5 minutes to one hour. Examination of these papers by scanning electron microscopy indicates that vesicles remain on the surface of the paper after incubation in water for up to one hour. Papers made using 1-palmitoyl-2-(10,12-tricosadiynoyl)-sn-glycero-3-phosphocholine that was not crosslinked steadily lose vesicles over the course of a one-hour incubation in water.

In another test for strength of attachment, after deposition and polymerization of 1-palmitoyl-2-(10,12-tricosadiynoyl)-sn-glycero-3-phosphocholine on a substrate, the substrate is placed in water and subjected to fluid shear flow. Less vesicle loss is observed from papers containing vesicles made from crosslinked 1-palmitoyl-2-(10,12-tricosadiynoyl)-sn-glycero-3-phosphocholine, at both increased speed of flow and at increased time of flow at a constant speed, than is observed from papers made using 1-palmitoyl-2-(10,12-tricosadiynoyl)-sn-glycero-3-phosphocholine that was not crosslinked.

Example 2: Vesicle Formation on Nanopaper by Polymerization of a Diblock Copolymer 10 μL of a 1 mg/mL solution of a diblock copolymer consisting of 40 styrene and 50 3-(isocyano-1-alanyl-aminoethyl)-thiophene (PS-PIAT) in chloroform is placed onto circular pieces of nanocellulose paper 9.5 mm in diameter. The chloroform is allowed to evaporate. The nanopaper is incubated in 150 μL of water for 60 minutes; removed from the water, then exposed to 254 nm UV light for 20 minutes; using a small low-pressure mercury lamp (2 W, UVP, Pen-Ray, Upland, CA). The papers are then dried. Analysis of the dried papers by scanning electron microscopy shows that vesicles are present on the surface of the papers.

Papers are placed in water again and samples are removed at various time points from 5 minutes to one hour. Examination of these papers by scanning electron microscopy indicates that vesicles remain on the surface of the paper after incubation in water for up to one hour. Papers made using PS-PIAT that was not crosslinked steadily lose vesicles over the course of a one-hour incubation in water.

In another test for strength of attachment, after deposition and polymerization of PS-PIAT on a substrate, the substrate is placed in water and subjected to fluid shear flow. Less vesicle loss is observed from papers containing vesicles made from crosslinked PS-PIAT, at both increased speed of flow and at increased time of flow at a constant speed, than is observed from papers made using PS-PIAT that was not crosslinked.

Example 3: Vesicle Formation on Nanopaper by Polymerization of Lipid: 1,2-bis(10,12-tricosadiynoyl)-sn-glycero-3-phosphoethanolamine 10 μL of a 1 mg/mL solution of 1,2-bis(10,12-tricosadiynoyl)-sn-glycero-3-phosphoethanolamine in chloroform is placed onto circular pieces of nanocellulose paper 9.5 mm in diameter. The chloroform is allowed to evaporate. The nanopaper is incubated in 150 μL of water for 60 minutes; removed from the water, then exposed to 254 nm UV light for 20 minutes; using a small low-pressure mercury lamp (2 W, UVP, Pen-Ray, Upland, CA). The papers are then dried. Analysis of the dried papers by scanning electron microscopy shows that vesicles are present on the surface of the papers.

Papers are placed in water again and samples are removed at various time points from 5 minutes to one hour. Examination of these papers by scanning electron microscopy indicates that vesicles remain on the surface of the paper after incubation in water for up to one hour. Papers made using 1,2-bis(10,12-tricosadiynoyl)-sn-glycero-3-phosphoethanolamine that was not crosslinked steadily lose vesicles over the course of a one-hour incubation in water.

In another test for strength of attachment, after deposition and polymerization of 1,2-bis(10,12-tricosadiynoyl)-sn-glycero-3-phosphoethanolamine on a substrate, the substrate is placed in water and subjected to fluid shear flow. Less vesicle loss is observed from papers containing vesicles made from crosslinked 1,2-bis(10,12-tricosadiynoyl)-sn-glycero-3-phosphoethanolamine, at both increased speed of flow and at increased time of flow at a constant speed, than is observed from papers made using 1,2-bis(10,12-tricosadiynoyl)-sn-glycero-3-phosphoethanolamine that was not crosslinked.

Example 4: Vesicle Formation on Nanopaper by Polymerization of Lipid: 1-palmitoyl-2-(10,12-tricosadiynoyl)-sn-glycero-3-phosphoethanolamine 10 μL of a 1 mg/mL solution of 1-palmitoyl-2-(10,12-tricosadiynoyl)-sn-glycero-3-phosphoethanolamine in chloroform is placed onto circular pieces of nanocellulose paper 9.5 mm in diameter. The chloroform is allowed to evaporate. The nanopaper is incubated in 150 μL of water for 60 minutes; removed from the water, then exposed to 254 nm UV light for 20 minutes; using a small low-pressure mercury lamp (2 W, UVP, Pen-Ray, Upland, CA). The papers are then dried. Analysis of the dried papers by scanning electron microscopy shows that vesicles are present on the surface of the papers.

Papers are placed in water again and samples are removed at various time points from 5 minutes to one hour. Examination of these papers by scanning electron microscopy indicates that vesicles remain on the surface of the paper after incubation in water for up to one hour. Papers made using 1-palmitoyl-2-(10,12-tricosadiynoyl)-sn-glycero-3-phosphoethanolamine that was not crosslinked steadily lose vesicles over the course of a one-hour incubation in water.

In another test for strength of attachment, after deposition and polymerization of 1-palmitoyl-2-(10,12-tricosadiynoyl)-sn-glycero-3-phosphoethanolamine on a substrate, the substrate is placed in water and subjected to fluid shear flow. Less vesicle loss is observed from papers containing vesicles made from crosslinked 1-palmitoyl-2-(10,12-tricosadiynoyl)-sn-glycero-3-phosphoethanolamine, at both increased speed of flow and at increased time of flow at a constant speed, than is observed from papers made using 1-palmitoyl-2-(10,12-tricosadiynoyl)-sn-glycero-3-phosphoethanolamine that was not crosslinked.

Example 5: Vesicle Formation on Nanopaper by Polymerization of Lipid: 1,2-bis(10,12-tricosadiynoyl)-sn-glycero-3-phosphocholine 10 μL of a 1 mg/mL solution of 1,2-bis(10,12-tricosadiynoyl)-sn-glycero-3-phosphocholine in chloroform is placed onto circular pieces of nanocellulose paper 9.5 mm in diameter. The chloroform is allowed to evaporate. The nanopaper is incubated in 150 μL of water for 60 minutes; removed from the water, then exposed to 254 nm UV light for 20 minutes; using a small low-pressure mercury lamp (2 W, UVP, Pen-Ray, Upland, CA). The papers are then dried. Analysis of the dried papers by scanning electron microscopy shows that vesicles are present on the surface of the papers.

Papers are placed in water again and samples are removed at various time points from 5 minutes to one hour. Examination of these papers by scanning electron microscopy indicates that vesicles remain on the surface of the paper after incubation in water for up to one hour. Papers made using 1,2-bis(10,12-tricosadiynoyl)-sn-glycero-3-phosphocholine that was not crosslinked steadily lose vesicles over the course of a one-hour incubation in water.

In another test for strength of attachment, after deposition and polymerization of 1,2-bis(10,12-tricosadiynoyl)-sn-glycero-3-phosphocholine on a substrate, the substrate is placed in water and subjected to fluid shear flow. Less vesicle loss is observed from papers containing vesicles made from crosslinked 1,2-bis(10,12-tricosadiynoyl)-sn-glycero-3-phosphocholine, at both increased speed of flow and at increased time of flow at a constant speed, than is observed from papers made using 1,2-bis(10,12-tricosadiynoyl)-sn-glycero-3-phosphocholine that was not crosslinked.

Example 6: Vesicle Formation on Nanopaper by Polymerization of Lipid: 1,2-bis(11-mercaptoundecanoyl)-sn-glycero-3-phosphocholine 10 μL of a 1 mg/mL solution of 1,2-bis(11-mercaptoundecanoyl)-sn-glycero-3-phosphocholine in chloroform is placed onto circular pieces of nanocellulose paper 9.5 mm in diameter. The chloroform is allowed to evaporate. The nanopaper is incubated in 150 μL of water for 60 minutes; removed from the water, then exposed to 254 nm UV light for 20 minutes; using a small low-pressure mercury lamp (2 W, UVP, Pen-Ray, Upland, CA). The papers are then dried. Analysis of the dried papers by scanning electron microscopy shows that vesicles are present on the surface of the papers.

Papers are placed in water again and samples are removed at various time points from 5 minutes to one hour. Examination of these papers by scanning electron microscopy indicates that vesicles remain on the surface of the paper after incubation in water for up to one hour. Papers made using 1,2-bis(11-mercaptoundecanoyl)-sn-glycero-3-phosphocholine that was not crosslinked steadily lose vesicles over the course of a one-hour incubation in water.

In another test for strength of attachment, after deposition and polymerization of 1,2-bis(11-mercaptoundecanoyl)-sn-glycero-3-phosphocholine on a substrate, the substrate is placed in water and subjected to fluid shear flow. Less vesicle loss is observed from papers containing vesicles made from crosslinked 1,2-bis(11-mercaptoundecanoyl)-sn-glycero-3-phosphocholine, at both increased speed of flow and at increased time of flow at a constant speed, than is observed from papers made using 1,2-bis(11-mercaptoundecanoyl)-sn-glycero-3-phosphocholine that was not crosslinked.

Example 7: Vesicle Formation on Nanopaper by Polymerization of Lipid: 2 bis(tricosa-10,12-diynoyl)-sn-glycero-3-phosphocholine 10 μL of a 1 mg/mL solution of 2 bis(tricosa-10,12-diynoyl)-sn-glycero-3-phosphocholine in chloroform is placed onto circular pieces of nanocellulose paper 9.5 mm in diameter. The chloroform is allowed to evaporate. The nanopaper is incubated in 150 μL of water for 60 minutes; removed from the water, then exposed to 254 nm UV light for 20 minutes; using a small low-pressure mercury lamp (2 W, UVP, Pen-Ray, Upland, CA). The papers are then dried. Analysis of the dried papers by scanning electron microscopy shows that vesicles are present on the surface of the papers.

Papers are placed in water again and samples are removed at various time points from 5 minutes to one hour. Examination of these papers by scanning electron microscopy indicates that vesicles remain on the surface of the paper after incubation in water for up to one hour. Papers made using 2 bis(tricosa-10,12-diynoyl)-sn-glycero-3-phosphocholine that was not crosslinked steadily lose vesicles over the course of a one-hour incubation in water.

In another test for strength of attachment, after deposition and polymerization of 2 bis(tricosa-10,12-diynoyl)-sn-glycero-3-phosphocholine on a substrate, the substrate is placed in water and subjected to fluid shear flow. Less vesicle loss is observed from papers containing vesicles made from crosslinked 2 bis(tricosa-10,12-diynoyl)-sn-glycero-3-phosphocholine, at both increased speed of flow and at increased time of flow at a constant speed, than is observed from papers made using 2 bis(tricosa-10,12-diynoyl)-sn-glycero-3-phosphocholine that was not crosslinked.

Example 8: Comparison of Vesicle Yield and Vesicle Size Using Different Methods of Vesicle Formation Lipid Solutions A stock solution of DOPC:TopFluor-Cholesterol 99.5:0.5 mol % lipid was prepared in neat chloroform at a concentration of 10 mg/mL Working solutions having a concentration of 1 mg/mL were prepared from this stock solution. Stock solutions and working solutions were stored in a glass vial purged with argon and capped with a Teflon lined cap in a −20° C. freezer until use.

Deposition of Lipids

Circular disks with a diameter of 9.5 mm were punched out from cleaned nanocellulose paper, tracing paper, and regenerated cellulose dialysis membrane, using a circle hole punch (EK Tools Circle Punch, ⅜ in.). 10 µL of the working solution of lipid (1 mg/mL) was deposited using a glass syringe (Hamilton) onto the papers. For gentle hydration and electroformation, 10 µL of the working lipid solution was spread onto a 9.5 mm diameter circular area on the substrates. A 9.5 mm diameter paper cutout, placed on the back surface of the slides, served as guide for spreading the lipid. After deposition of lipid solution, all substrates were placed into a standard laboratory vacuum desiccator for a minimum of 1 hour to remove traces of solvent before proceeding to the growth stage.

Vesicle Growth by Gentle Hydration on Paper

Dry, solvent-free lipid-coated substrates (nanocellulose paper, tracing paper and regenerated cellulose dialysis membrane) were placed into individual wells in a 48-well plate. With a pipette, 150 µL of the hydrating solution (100 mM sucrose in water) was added to the bottom corner of the well to fully immerse the substrate in solution. The 48-well plate was then covered with a lid and the lipid-coated papers were allowed to incubate in the growth buffer for 1 hour.

Vesicle Growth by Gentle Hydration on Glass

Circular PDMS gaskets (inner diameter×height=12×1 mm) were affixed to a glass microscope slide to construct a barrier around the dry solvent-free lipid films. 150 µL of the hydrating solution (100 mM sucrose) was added into the chamber formed by the gasket, then a glass cover slip was carefully placed on top of the gasket, sealing the chamber; and the film was allowed to hydrate for 1 hour.

Vesicle Growth by Electroformation

Established protocols were used to prepare GUVs by electroformation. Collins et al. (2013) *JoVE*, No. 76, e50227; Li et al. (2016) *Colloids Surfaces B Biointerfaces*, 147:368-375; Herold et al. (2012) *Langmuir* 28:5518-5521.

Briefly, circular PDMS gaskets (inner diameter×height=12×1 mm) were affixed to a glass microscope slide coated with indium tin oxide (ITO) to construct a barrier around the dry solvent-free lipid film. 150 µL of hydrating solution (100 mM sucrose) was added into the chamber formed by the gasket, and a second ITO-coated glass slide was placed atop the gasket to form a closed chamber. The ITO surfaces were connected to the leads of a function generator (33120A Agilent) with conductive copper tape; and a sinusoidal AC field at a field strength of 1.5 V/mm peak-to-peak and frequency of 10 Hz was applied for 1 hour.

Harvesting of Vesicles

For the gentle hydration and electroformation methods (that use a PDMS ring and a top slide or cover slip) the chambers were disassembled by carefully removing the top cover. For techniques that used a 48-well plate (gentle hydration on nanopaper, tracing paper, and regenerated cellulose membranes) no disassembly was required. GUVs made by all methods were harvested by gently aspirating 100 µL of the hydrating solution into a cut 1000 µL pipette tip. This procedure was repeated exactly 6 times on different regions to cover the entire substrate. On the final repetition, all of the liquid (~ 150 µL) containing the GUVs was aspirated and transferred into a microcentrifuge tube (Eppendorf). Aliquots were removed immediately for imaging.

Stopped Growth

For stopped growth (i.e., time-course) experiments, lipid-coated substrates were prepared as described above and samples were harvested from the hydrating solution at different time points including 1 minute, 5 minutes, 10 minutes, 30 minutes, and 120 minutes.

Confocal Microscopy of Harvested Vesicles

Imaging chambers were constructed by covalently bonding custom-made PDMS gaskets with a square opening (width×length×height=6×6×1 mm) to glass microscope slides. Before use, the chamber was passivated with a solution of 1 mg/mL casein to prevent rupture of the GUVs on the bare glass. Faysal et al. (2017) *PLoS One* 12:1-16. The passivated chamber was filled with 58 µL of an isomolar solution of glucose and a 2 µL aliquot of a suspension of harvested GUVs was added. The GUVs were allowed to sediment for 3 hours before imaging.

Images were captured using an upright confocal laser-scanning microscope (LSM 880, Axio Imager.Z2m, Zeiss, Germany). Samples were excited with a 488 nm argon laser and TopFluor® fluorescence was visualized using a 10× Plan-Apochromat objective with a numerical aperture of 0.45. The entire area of the chamber was imaged using an automated tile scan routine (64 images [850.19 µm×850.19 µm (3212 pixels×3212 pixels)]). The routine used an autofocus feature at each tile location. The pinhole was set at 12.66 Airy Units which provided a confocal slice thickness of 80 µm.

Image Processing and Data Analysis

Confocal tilescan images were analyzed using a custom MATLAB routine8 (Mathworks Inc., Natick, MA). The routine thresholded the images and then applied a watershed algorithm to segment the fluorescent objects from the background. The native regionprops function was used to obtain the equivalent diameters and mean intensity of the segmented objects. GUVs were selected from the detected objects based on intensity. Pazzi et al. (2018) *Langmuir* 35:7798-7804. GUVs fall within 1-3 times the full width at half the maximum (FWHM) of the highest peak in the intensity histogram. Once selected, MATLAB native routines were used to obtain histograms of diameters of the GUVs, calculate the fractional yield and perform statistical tests.

Calculation of Molar Yield

The moles of lipid in N GUVs from a harvested suspension were determined using Equation 1.

$$\text{mol}_{GUV} = \frac{2\pi V_h}{N_A A_{hg} V_{al}} \sum_{i=1}^{N} (d_i)^2 \quad (1)$$

In this equation, $N_A$ is Avagadro's number, $A_{hg}$ is the lipid headgroup area, $V_h$ is the volume of the harvested suspension, $V_{al}$ is the volume of the aliquot, and $d_i$ is the diameter of vesicle i. The factor of 2 accounts for the fact that 2 lipid leaflets are present in a bilayer. The molar yield of GUVs of a given diameter can be obtained by summing only the GUVs of a specific diameter. For ease of analysis, GUVs can be divided into three size ranges: small GUVs ($1 \leq d_i < 10$), large GUVs ($10 \leq d_i < 50$) and very large GUVs ($d_i \geq 50$).

$$mol_{GUV} = mol_{small\ GUVs} + mol_{large\ GUVs} + mol_{GUVs \geq 50} \quad (2)$$

$$mol_{GUV} = \frac{2\pi V_h}{N_A A_{hg} V_{al}} \left( \sum_{i=1}^{N_d < 10} (d_i)^2 + \sum_{i=d \geq 10}^{N_d < 50} (d_i)^2 + \sum_{i=d \geq 50}^{N} (d_i)^2 \right) \quad (3)$$

To estimate the total amount of lipids present in the harvested population, $mol_{tot}$, the harvested solution was solubilized with the surfactant Triton X-100. To this end, 50 μL of the harvested solution was mixed with 50 μL of a solution of Triton X-100 (at a concentration of 3 mM) to obtain a final concentration of Triton X-100 of 1.5 mM (concentration ~0.1 w/w %, the critical micelle concentration (CMC) of Triton X-100 is 0.22-0.24 mM). The solution was incubated for 1 hour at room temperature, then fluorescence intensity was measured using a SpectraMax M2e plate reader (Molecular Devices) and the fluorescence intensity values were converted to the amount of lipid using a calibration curve. The molar yield, $Y_{mol}$, of GUVs was obtained using Equation 4:

$$Y_{mol} = \frac{mol_{GUV}}{mol_{tot}} * 100\% \quad (4)$$

Statistical Tests

All statistical tests were performed in MATLAB. For statistical testing, the groups were assigned by technique, as follows. Group 1: Gentle hydration on glass, Group 2: Gentle Hydration on Regenerated Cellulose Dialysis Membranes, Group 3: Gentle Hydration on Nanopaper, Group 4: Gentle Hydration on Tracing Paper, Group 5: Electroformation. There were five independent repeats within each group. Statistical significance of differences in the mean molar yields were determined by performing a balanced one-way Analysis of Variance (ANOVA) followed by a post-hoc Tukey honestly significant test (HSD). An ANOVA assumes that the repeats drawn for each group have a normal distribution and that the variances between each group are equal. An Anderson Darling test was conducted to determine normality. The results of the test are shown in Table 3. All repeats within a group were consistent with being drawn from a normal distribution. A Bartlett's test was also conducted to determine if the variances of the groups were equal, and results of the tests, shown in Table 3, indicate that the variances between groups were equal. Thus, the data satisfy the criteria for an ANOVA. The ANOVA table and post-hoc HSD tables are shown in Table 4, and summaries of the conclusions are provided at the end of that table.

Results

Vesicles were formed by gentle hydration on a glass substrate, by electroformation on an ITO-coated glass substrate, and by gentle hydration according to the methods described herein on regenerated cellulose, tracing paper and nanopaper. Size and yield of GUVs were measured over a period of two hours, at time points of 1, 5, 10, 30, 60 and 120 minutes. As shown in Table 5 and FIGS. 2A-2D, both molar yield of vesicles and percentage of large vesicles were higher on the paper substrates. FIGS. 3A-3D show histograms of vesicle size using the four different methods, again indicating that larger vesicles are obtained using paper substrates (compared to glass) and, in particular, nanofibers yield larger vesicles than do fibers having flatter, smoother surfaces, such as regenerated cellulose.

Figure 5:
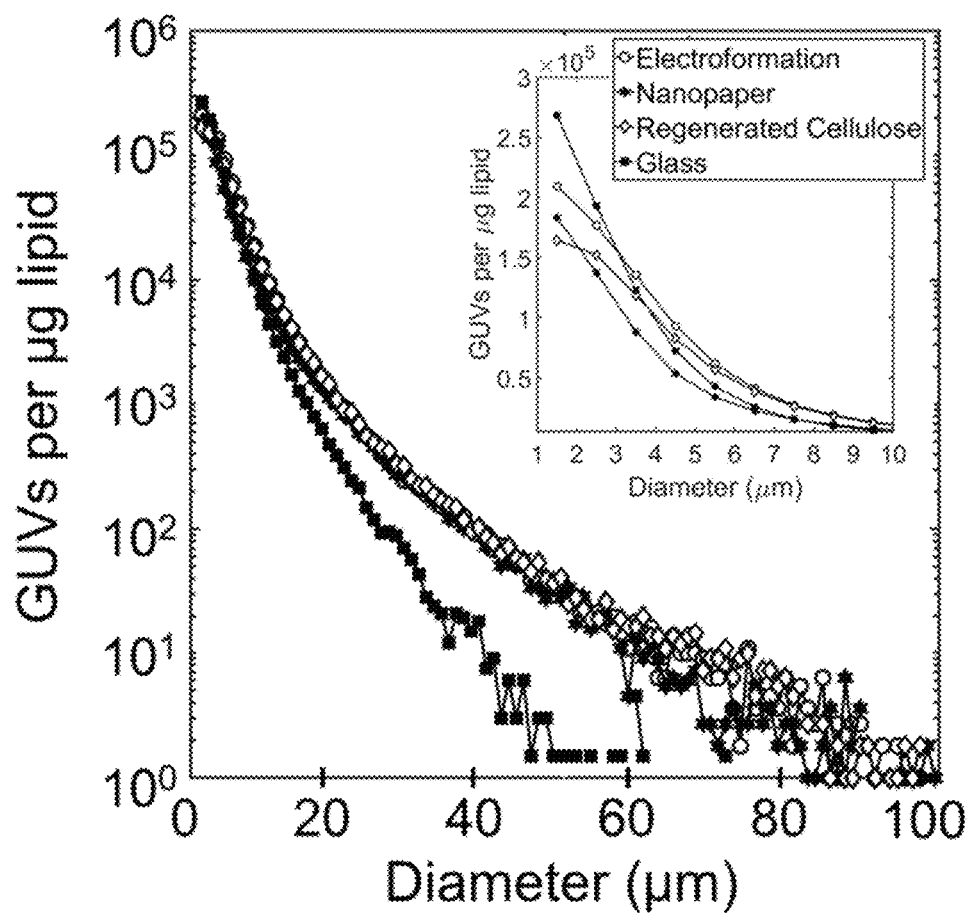
FIG. 5 shows histograms of the distribution of sizes of GUVs harvested after 60 minutes on nanocellulose paper, regenerated cellulose, by electroformation, and by gentle hydration on glass. The solid dots represent the average normalized counts of GUVs (n=5) harvested from each substrate with bin widths of 1 micrometer. The GUV counts are normalized per microgram of lipid harvested. The transparent lines show the histograms for the individual replicates for each substrate. Note the logarithmic scaling of the y-axis. The inset shows a zoom of the histograms from 1-10 micrometers on a linear scaling. Only the averages are plotted for ease of viewing.

Molar yield of lipid in vesicles harvested after 60 minutes of growth was determined. As shown in FIG. 4, the use of nanopaper and tracing paper provides both higher yields and higher fraction of larger vesicles than do other substrates. Histograms of vesicle diameter are shown in FIG. 5, again confirming that GUVs grown on nanopaper are larger than those grown on other substrates.

TABLE 3

Anderson Darling and Bartlett tests indicate assumption criteria for valid ANOVA testing are met

|  | Value | Nano-paper | Tracing Paper | Glass | Electro-formation | Regenerated Cellulose |
|---|---|---|---|---|---|---|
| Anderson Darling | p | 0.9857 | 0.5215 | 0.6985 | 0.536 | 0.4447 |
| Bartlett's Test | p |  |  | 0.1766 |  |  |

TABLE 4

ANOVA table and table of p-values from posthoc Tukey HSD tests of the mean molar yields of GUVs obtained from gentle hydration on nanocellulose paper, gentle hydration on tracing paper, gentle hydration on glass, electroformation, and gentle hydration on regenerated cellulose.

| Source | SS | df | MS | F | Prob > F, (p-value) |
|---|---|---|---|---|---|
| Columns | 2204.55 | 4 | 551.139 | 40.58 | 2.50E−09 |
| Error | 271.64 | 20 | 13.582 |  |  |
| Total | 2476.19 | 24 |  |  |  |

| Group 1 | Group 2 | p-value | Significance | Comments |
|---|---|---|---|---|
| Nanopaper | Glass | 1.38E−07 | *** | Effect of curvature significant |
| Nanopaper | Electroformation | 7.14E−06 | *** | Effect of curvature significant |
| Nanopaper | Regenerated Cellulose | 6.43E−06 | *** | Effect of curvature significant |
| Nanopaper | Tracing Paper | 0.972 | NS | Effect of manufacturing paper not significant |

TABLE 4-continued

ANOVA table and table of p-values from posthoc Tukey HSD tests of the mean molar yields of GUVs obtained from gentle hydration on nanocellulose paper, gentle hydration on tracing paper, gentle hydration on glass, electroformation, and gentle hydration on regenerated cellulose.

| Source | | SS | df | MS | F | Prob > F, (p-value) |
|---|---|---|---|---|---|---|
| Tracing Paper | Glass | 5.46E−08 | | | *** | Effect of curvature significant |
| Tracing Paper | Electroformation | 2.11E−06 | | | *** | Effect of curvature significant |
| Tracing Paper | Regenerated Cellulose | 1.91E−06 | | | *** | Effect of curvature significant |
| Glass | Electroformation | 0.258 | | | NS | Effect of electric field not significant |
| Glass | Regenerated Cellulose | 0.279 | | | NS | Effect of permeability not significant |
| Electroformation | Regenerated Cellulose | 0.999 | | | NS | Effect of electric field not significant |

NS not significant, $*p < 0.05$, $p < 0.01$ $*p < 0.001$

TABLE 5

Molar yield (%) of lipid harvested as GUVs at 1 minute, 5 minutes, 10 minutes, 30 minutes, 60 minutes, and 120 minutes on the glass, electroformation, regenerated cellulose and tracing paper substrates. Averages and standard deviations were calculated from 3 replicate samples at each time point for each substrate.
Molar Yield % (Average ± Standard Deviation)

| | Glass | Electroformation | Regenerated Cellulose | Tracing Paper |
|---|---|---|---|---|
| 1 minute | 11.5 ± 2.0 | 8.2 ± 4.9 | 9.8 ± 2.4 | 16.2 ± 1.8 |
| 5 minutes | 10.5 ± 2.2 | 12.5 ± 2.7 | 15.7 ± 1.6 | 24.0 ± 2.3 |
| 10 minutes | 12.6 ± 2.8 | 10.7 ± 3.3 | 19.6 ± 4.5 | 30.0 ± 4.0 |
| 30 minutes | 12.5 ± 3.9 | 15.8 ± 5.8 | 21.5 ± 1.2 | 37.5 ± 2.1 |
| 60 minutes | 16.3 ± 2.0 | 21.1 ± 1.5 | 21.2 ± 3.4 | 39.1 ± 4.7 |
| 120 minutes | 15.6 ± 2.1 | 20.6 ± 1.5 | 19.7 ± 2.0 | 36.3 ± 2.2 |

Example 9: Determination of Optimal Lipid Concentration for Maximal Yield of Vesicles Vesicles were formed on nanopaper using four different amphiphiles at various concentrations to determine the concentration of each amphiphile that provides maximal yield of vesicles.

Vesicle Formation

Four different lipids—DOPC (1,2-dioleoyl-sn-glycero-3-phosphocholine), DOPG (1,2-dioleoyl-sn-glycero-3-phospho-(1'-rac-glycerol), DOTAP (1,2-dioleoyl-3-trimethylammonium-propane) and DOPC doped with 5 mol % PEG-2k-PE (1,2-dioleoyl-sn-glycero-3-phosphoethanolamine-N-[methoxy(polyethylene glycol)-2000) were tested at a range of surface concentrations. All lipids were doped with 0.5 mol % Top-Fluor Cholesterol (23-(dipyrrometheneboron difluoride)-24-norcholesterol) to enable viewing of the vesicles using a confocal microscope.

For each experiment, 10 µL of lipid, dissolved in chloroform, was deposited on a circular piece of nanopaper (tracing paper) that was 9.5 mm in diameter. For DOPC, the values of lipid mass per surface area were 71 mg/m$^2$, 141 mg/m$^2$, 282 mg/m$^2$, and 1411 mg/m$^2$. For DOPG, values of lipid mass per area of substrate were 71 mg/m$^2$, 141 mg/m$^2$, 353 mg/m$^2$, 705 mg/m$^2$, and 1411 mg/m$^2$. For DOTAP, values of lipid mass per area of substrate were 141 mg/m$^2$, 353 mg/m$^2$, 705 mg/m$^2$, and 1411 mg/m$^2$. For DOPC doped with 5 mol % PEG-2k-PE, values of lipid mass per area of substrate were 141 mg/m$^2$, 282 mg/m$^2$, 705 mg/m$^2$, and 1411 mg/m$^2$.

After the lipids were deposited on the surface of the paper, the excess chloroform was allowed to evaporate away in a fume hood. The paper was then placed under vacuum for 1 hour to drive off any residual solvent. To produce vesicles, the lipid covered substrate was placed in a 48-well plate and hydrated in a 100 mM sucrose solution for 1 hour. During this period, the lipid stacks on the surface of the paper swell and bud off to form vesicles, most of which were attached to the paper via nanotubes. A 1000 µL pipette with its tip cut off was used to harvest the vesicles by gently aspirating the surface of the paper 6 times. The vesicles were stored in a microcentrifuge tube (Eppendorf) before imaging.

Imaging

The GUVs were imaged in custom-made square chambers of poly(dimethylsiloxane) with dimensions (width×length× height) of 6 mm×6 mm×1 mm that were covalently bonded to a microscope slide. The chambers were passivated with 1 mg/mL casein dissolved in 1×PBS for imaging vesicles made from DOPC, DOPG and PEG-2k-PE, and with 1 mg/mL of poly-L-lysine hydrochloride dissolved in water for DOTAP vesicles.

An aliquot of the GUV solution was deposited in the imaging chamber, with the volume adjusted to obtain between 100,000 to 150,000 objects in the imaging plane. An isomolar solution of 100 mM glucose was then added, to bring the total volume of solution in the chamber to 60 µL. The sucrose-filled vesicles are denser and therefore, sink to the bottom of the chamber. The vesicles were imaged after 3 hours of sedimentation, using a confocal laser scanning microscope (LSM 880 with Airyscan+FAST, Axio Imager.Z2m, Zeiss, Germany). The bottom of the entire chamber was imaged using an automated tilescan routine that produces 64 images (3212×3212 pixels per image, 850.19 m×850.19 µm).

Results

Figure 6:
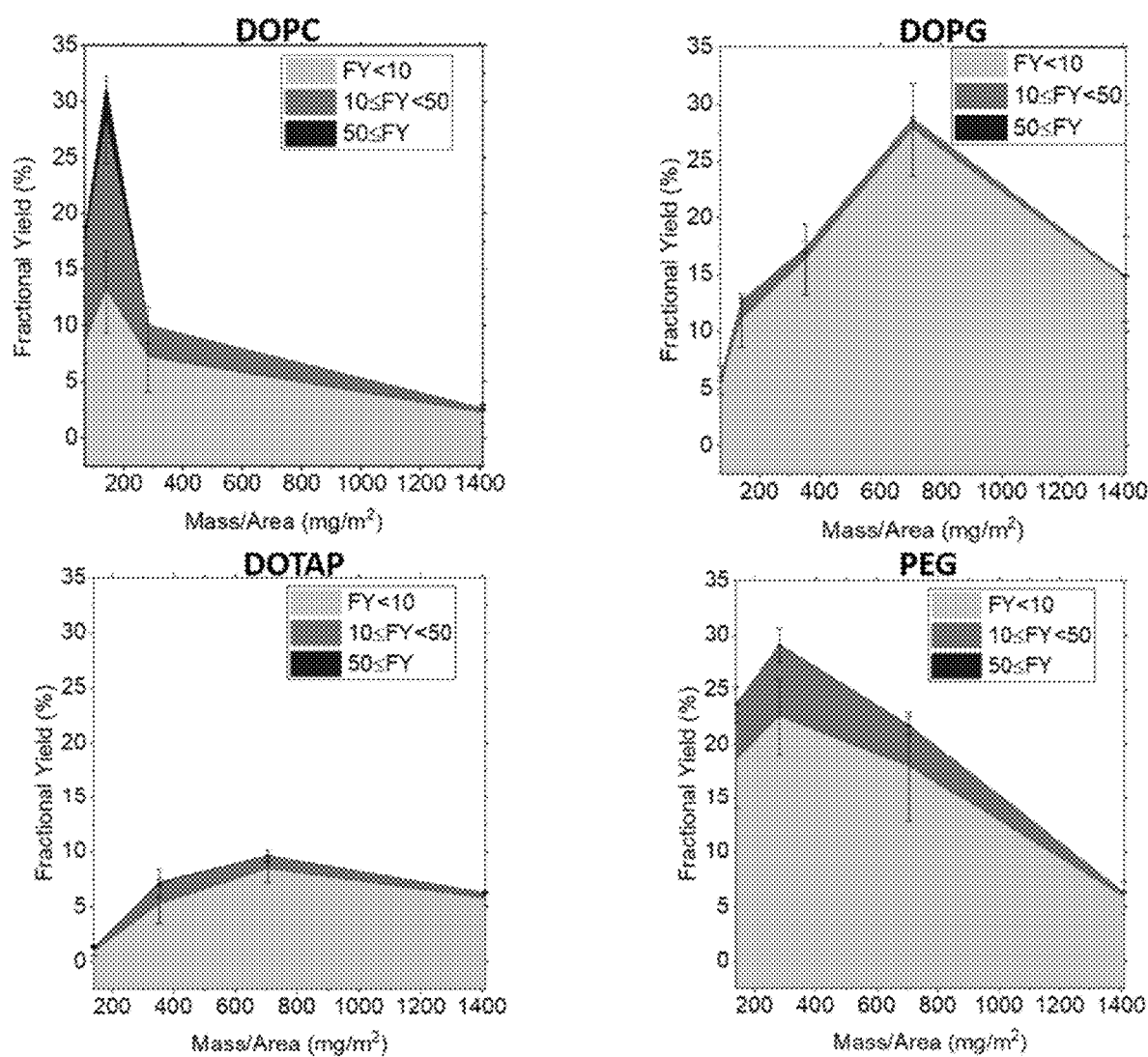
FIG. 6 shows fractional yields of vesicles, as a function of lipid concentration per unit area of substrate, for four different lipids. Shading represents the contribution of small (light shading), medium (intermediate shading) and large (dark shading) sizes to the fractional yield.

Concentrations of each lipid optimal for maximum yield of vesicles were determined by measuring fractional yield of vesicles (determined as described in Example 8 at different lipid concentrations. The results are shown in FIG. 6. Confocal images of the vesicles formed from low, optimal and high concentrations of each lipid are shown in FIGS. 7A-7D. Optimal concentrations for each of the lipids are 1 mg/mL for DOPC, 5 mg/mL for DOPG, 5 mg/ml for DOTAP and 2 mg/mL for PEG-2k-PE.

What is claimed is:

1. A method for making a vesicle-coated substrate, the method comprising:
   (a) dispersing an amphiphilic molecule in a solvent, wherein the amphiphilic molecule contains a crosslinkable moiety, wherein the crosslinkable moiety is selected from the group consisting of tricosadiynoyl, thiophene, 11-mercaptoundecanoyl, methacrylate and diacetylenyl monomer;
   (b) contacting the dispersed amphiphilic molecule of (a) with the substrate;
   (c) removing the solvent;
   (d) incubating the amphiphile-coated substrate in a first aqueous solution; and
   (e) subjecting the amphiphile-coated substrate to conditions under which the amphiphilic molecules are crosslinked.

2. The method of claim 1, wherein the amphiphilic molecule is a phospholipid, a sphingolipid, a fatty acid, a quaternary ammonium surfactant, a ceramide, a fatty alcohol, a amphiphilic polymer, a diblock polymer or a triblock polymer.

3. The method of claim 1, wherein the solvent is chloroform, methanol, ethanol, isopropanol or water.

4. The method of claim 1, wherein the substrate comprises an element having at least one principal radius of curvature that is not zero.

5. The method of claim 4, wherein the substrate is a fiber.

6. The method of claim 5, wherein the fiber is a naturally-occurring fiber.

7. The method of claim 6, wherein the fiber is cellulose, silk or wool.

8. The method of claim 7, wherein the cellulose is cotton, hemp or jute.

9. The method of claim 7, wherein the cellulose is papyrus, paper or wood pulp.

10. The method of claim 9, wherein the fiber is a synthetic fiber.

11. The method of claim 10, wherein the fiber is nylon, polyester or fiberglass.

12. The method of claim 5, wherein the fiber is a semi-synthetic fiber.

13. The method of claim 12, wherein the semi-synthetic fiber is rayon.

14. The method of claim 5, wherein the fiber is a nanofiber.

15. The method of claim 14, wherein the nanofiber is tracing paper, nanocelluose paper, regenerated cellulose membrane, polycaprolactone, collagen, or decellularized extracellular matrix.

16. The method of claim 15, wherein the nanocellulose paper is made by solution casting of nanocellulose pulp.

17. The method of claim 5, wherein the fiber is a metal mesh.

18. The method of claim 1, wherein the first aqueous solution has an ionic strength of less than 10 mM monovalent salt.

19. The method of claim 18, further comprising the step of:
   (e) increasing the ionic strength of the first aqueous solution.

20. The method of claim 19, wherein step (d) is conducted for 10 minutes.

21. The method of claim 1, further comprising, prior to step (d), introducing a compound into the first aqueous solution.

22. The method of claim 1, further comprising, in step (a), dispersing a second molecule in the solvent.

23. The method of claim 22, wherein the second molecule is hydrophilic and the solvent is water.

24. The method of claim 1, wherein the solvent is removed by evaporation.

25. A vesicle-coated substrate made by the method of claim 1.

26. The substrate of claim 25, wherein the vesicles are unilamellar.

27. The substrate of claim 25, wherein the vesicles are multilamellar.

28. A therapeutic composition comprising the vesicle-coated substrate of claim 25, wherein the vesicle-coated substrate further comprises one or more therapeutic molecules.

29. A cosmetic composition comprising the vesicle-coated substrate of claim 25, wherein the vesicle-coated substrate further comprises one or more cosmetic molecules.

30. A method of applying a therapeutic composition to a subject, the method comprising contacting the subject with the therapeutic composition of claim 28.

31. A method of applying a cosmetic composition to a subject, the method comprising contacting the subject with the cosmetic composition of claim 29.

32. The method of claim 1, wherein said conditions under which the amphiphilic molecules are crosslinked is irradiation with ultraviolet light.

* * * * *